US011136387B2

(12) United States Patent
Yang et al.

(10) Patent No.: US 11,136,387 B2
(45) Date of Patent: Oct. 5, 2021

(54) IL-13 ANTIBODY AND PREPARATION METHOD AND USE THEREOF

(71) Applicant: SHANGHAI PHARMAEXPLORER CO., LTD., Shanghai (CN)

(72) Inventors: Yizhen Yang, Shanghai (CN); Shiyong Gong, Shanghai (CN); Lijuan Hao, Shanghai (CN); Jian Wu, Shanghai (CN); Xinxiu Yang, Shanghai (CN); Qin Zhong, Shanghai (CN); Shaoping Hu, Shanghai (CN); Stewart Leung, Shanghai (CN); Qing Duan, Shanghai (CN); Lile Liu, Shanghai (CN)

(73) Assignee: SHANGHAI PHARMAEXPLORER CO., LTD., Shanghai (CN)

( * ) Notice: Subject to any disclaimer, the term of this patent is extended or adjusted under 35 U.S.C. 154(b) by 0 days.

(21) Appl. No.: 16/302,396

(22) PCT Filed: May 16, 2017

(86) PCT No.: PCT/CN2017/084553
§ 371 (c)(1),
(2) Date: Nov. 16, 2018

(87) PCT Pub. No.: WO2017/198148
PCT Pub. Date: Nov. 23, 2017

(65) Prior Publication Data
US 2019/0309059 A1 Oct. 10, 2019

(30) Foreign Application Priority Data

May 18, 2016 (CN) .......... 201610333020.X
Jun. 24, 2016 (CN) .......... 201610474103.0

(51) Int. Cl.
| C07K 16/24 | (2006.01) |
| A61K 39/395 | (2006.01) |
| G01N 33/68 | (2006.01) |
| C12N 15/85 | (2006.01) |
| C07K 16/06 | (2006.01) |
| A61K 39/00 | (2006.01) |

(52) U.S. Cl.
CPC .......... *C07K 16/244* (2013.01); *A61K 39/395* (2013.01); *C07K 16/065* (2013.01); *C07K 16/24* (2013.01); *C12N 15/85* (2013.01); *G01N 33/68* (2013.01); *G01N 33/6869* (2013.01); *A61K 2039/505* (2013.01); *C07K 2317/56* (2013.01); *C07K 2317/565* (2013.01); *C07K 2317/76* (2013.01); *C12N 2015/8518* (2013.01); *G01N 2333/5437* (2013.01)

(58) Field of Classification Search
None
See application file for complete search history.

(56) References Cited

U.S. PATENT DOCUMENTS

| 4,816,567 A | 3/1989 | Cabilly et al. |
| 5,225,539 A | 7/1993 | Winter |
| 5,866,363 A | 2/1999 | Pieczenik |
| 7,807,788 B2 | 10/2010 | Ashman et al. |
| 7,994,302 B2 | 8/2011 | Foltz et al. |
| 8,992,916 B2 | 3/2015 | Campbell et al. |
| 9,856,317 B2 | 1/2018 | Monk et al. |
| 2019/0309059 A1 | 10/2019 | Yang et al. |

FOREIGN PATENT DOCUMENTS

| CN | 107400165 A | 11/2017 |
| JP | 2007537702 A | 12/2007 |
| JP | 2008511542 A | 4/2008 |
| JP | 2008520684 A | 6/2008 |
| JP | 2009512656 A | 3/2009 |
| WO | 2005007699 A2 | 1/2005 |
| WO | 2006003407 A2 | 1/2006 |
| WO | 06055638 A2 | 5/2006 |
| WO | 2007045477 A2 | 4/2007 |
| WO | 17189805 A1 | 11/2017 |

OTHER PUBLICATIONS

Goldsby, Immunology, 5th edition, 2003, pp. 82-84.*
Rudikoff, et al. (Proc. Natl. Acad. Sci. USA, 79(6): 1979-1983, 1982.*
Brummell et al. (Biochemistry 32:1180-1187 (1993)).*
Kobayashi et al. (Protein Engineering 12:879-844 (1999)).*
Brorson et al. (J. Immunol. 163:6694-6701 (1999)).*
Coleman (Research in Immunol. 145:33-36 (1994)).*
Paul, Fundamental Immunology, 3rd Edition, 1993, pp. 292-295.*
Casset et al Biochemical and Biophysical Research Communications, 307:198-205, 2003.*
International Search Report of PCT/CN2017/084553 dated Aug. 9, 2017 (English Version).
Written Opinion of PCT/CN2017/084553 dated Aug. 9, 2017 (English Version).
May et al., "Strategies targeting the IL-4/IL13 axes in disease", Cytokine 75, 2015, p. 89-116.

(Continued)

*Primary Examiner* — Bridget E Bunner
*Assistant Examiner* — Fozia M Hamud
(74) *Attorney, Agent, or Firm* — Millen White Zelano & Branigan; Diana Hamlet-Cox

(57) ABSTRACT

The present invention discloses IL-13 antibody, method of its preparation and use thereof. The IL-13 antibody comprises one or more of heavy chain CDR1, heavy chain CDR2 and heavy chain CDR3 of heavy chain variable region of the IL-13 antibody, and/or one or more of light chain CDR1, light chain CDR2, and light chain CDR3 of light chain variable region of the IL-13 antibody. The IL-13 antibody has a high affinity and can significantly inhibit the secretion of thymus activation-regulated chemokine and periostin as well as the expression of vascular cell adhesion molecule-1 induced by IL-13, it can significantly inhibit airway hyper-responsiveness in mice induced by IL-13, and therefore can be used in the preparation of drugs for preventing or treating IL-13 expression or dysfunction related diseases.

12 Claims, 9 Drawing Sheets

Specification includes a Sequence Listing.

(56) References Cited

OTHER PUBLICATIONS

Kohler et al., "Continuous cultures of fused cells secreting antibody of predefined specificity", Nature vol. 256, 1975, p. 495-497.
Smith, "Filamentous fusion phage : novel expression vectors that display cloned antigens on the virion surface", Science, vol. 228, 1985, p. 1315-1317.
Sambrook, J., Fritsch, E. F., and Maniatis T. (1989) . Molecular Cloning: A Laboratory Manual, Second Edition (Plainview, New York: Cold Spring Harbor Laboratory Press) see summary TIBTECH—Jun. 1991 (vol. 9)pp. 213-214.
Miller et al., "Development of an in vitro potency bioassay for therapeutic IL-13 antagonists: The A-549 cell bioasaay",J Immunol Methods vol. 334, 2008, p. 134-141.
Bradford, "A rapid and sensitive method for the quantitation of microgram quantities of protein utilizing the principle of protein-dye binding", Anal Biochem vol. 72, 1976, p. 248-254.
McCafferty et al., "Phage antibodies: flamentous phage displaying antibody variable domains", Nature, vol. 348,1990, p. 552-554.
Cohen et al. "Reconstituting channels into planar membranes: A conceptual framework and methods for fusing vesicles to planar bilayer phospholipid membranes", Methods in Enzymology, vol. 220,1993.
Berkner, "Expression of heterologous sequences in adenoviral vectors", Current Topics in Microbiology and Immunology, vol. 158, Springer Verlag (1992), p. 39-66.
Griffiths et al., "Isolation of high affinity human antibodies directly from large synthetic repertoires", The EMBO Journal, 1994(14), vol. 13, p. 3245-3260.
Kieleczawa et al., "Optimization of protocol for sequencing of difficult templates", Journal of Biomolecular Techniques, 21, 2010, p. 97-102.
GenBank database, accession No. AAK53823.1 (1 Page), Mar. 2009.
Scott et al., "Searching for peptide ligands with an epitope library", Science,vol. 249, 1990, p. 386-390.
Hao et al., "The treatment of anti-IL-13 monoclonal antibody in bronchial asthma", International Journal of Respiration, vol. 34, No. 23, 2014, p. 1799-1802 (English abstract).
Tian et al., "Effects of IL-13 neutralization antibody on airway inflammation and Th1/Th2 cell function during convalescent period of asthma in mice", Immunological Journal, vol. 22, No. 3, 2006, p. 302-304 (English abstract).
Wen et al., "Effects of IL-13 neutralization antibody on airway inflammation in mice bronchial asthma model", Journal of China Medical University, vol. 42, No. 3, 2013, p. 249-252 (English abstract).
English translation of priority application No. CN 201610333020.X, Jun. 2017.
English translation of priority application No. CN 201610474103.0, Jun. 2017.
Supplementary EP search report in corresponding EP17798711 dated May 11, 2002 (pp. 1-15).
Scheerens H. et al., Clin. Exp. Allergy, Dec. 20, 2013, 44, p. 38-46.
Office action in corresponding Japanese Patent Application No. 2018-560916 dated May 11, 2021 (pp. 1-6)-English.

\* cited by examiner

SEQUENCE LISTING

<160> NUMBER OF SEQ ID NOS: 65

<210> SEQ ID NO 1
<211> LENGTH: 127
<212> TYPE: PRT
<213> ORGANISM: Artificial sequence
<220> FEATURE:
<223> OTHER INFORMATION: P4_4H12 heavy chain variable region

<400> SEQUENCE: 1

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Pro Val Gly Tyr Cys Ser Gly Gly Ser Cys Tyr Tyr Tyr
                100                 105                 110

Gly Met Asp Val Trp Gly Gln Gly Thr Thr Val Thr Val Ser Ser
            115                 120                 125

<210> SEQ ID NO 2
<211> LENGTH: 5
<212> TYPE: PRT
<213> ORGANISM: Artificial sequence
<220> FEATURE:
<223> OTHER INFORMATION: P4_4H12 heavy chain CDR1

<400> SEQUENCE: 2

Ser Tyr Ala Met His
 1               5

<210> SEQ ID NO 3
<211> LENGTH: 17
<212> TYPE: PRT
<213> ORGANISM: Artificial sequence
<220> FEATURE:
<223> OTHER INFORMATION: P4_4H12 heavy chain CDR2

<400> SEQUENCE: 3

Val Ile Ser Tyr Asp Gly Ser Asn Lys Tyr Tyr Ala Asp Ser Val Lys
 1               5                  10                  15

Gly

<210> SEQ ID NO 4
<211> LENGTH: 18
<212> TYPE: PRT
<213> ORGANISM: Artificial sequence
<220> FEATURE:
<223> OTHER INFORMATION: P4_4H12 heavy chain CDR3

<400> SEQUENCE: 4

Asp Pro Val Gly Tyr Cys Ser Gly Gly Ser Cys Tyr Tyr Tyr Gly Met
 1               5                  10                  15

Asp Val

<210> SEQ ID NO 5
<211> LENGTH: 108
<212> TYPE: PRT
<213> ORGANISM: Artificial sequence
<220> FEATURE:
<223> OTHER INFORMATION: P4_4H12 light chain variable region

<400> SEQUENCE: 5

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Asn Arg Ala Thr Gly Ile Pro Asp Arg Phe Tyr
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Thr Phe Gly Leu Gly Thr Lys Val Val Ile Lys
            100                 105

<210> SEQ ID NO 6
<211> LENGTH: 12
<212> TYPE: PRT
<213> ORGANISM: Artificial sequence
<220> FEATURE:
<223> OTHER INFORMATION: P4_4H12 light chain CDR1

<400> SEQUENCE: 6

Arg Ala Ser Gln Ser Val Ser Ser Ser Tyr Leu Ala
1               5                   10

<210> SEQ ID NO 7
<211> LENGTH: 7
<212> TYPE: PRT
<213> ORGANISM: Artificial sequence
<220> FEATURE:
<223> OTHER INFORMATION: P4_4H12 light chain CDR2

<400> SEQUENCE: 7

Gly Ala Ser Asn Arg Ala Thr
1               5

<210> SEQ ID NO 8
<211> LENGTH: 9
<212> TYPE: PRT
<213> ORGANISM: Artificial sequence
<220> FEATURE:
<223> OTHER INFORMATION: P4_4H12 light chain CDR3

<400> SEQUENCE: 8

Gln Gln Tyr Gly Ser Ser Pro Thr Thr
1               5

<210> SEQ ID NO 9
<211> LENGTH: 120
<212> TYPE: PRT
<213> ORGANISM: Artificial sequence
<220> FEATURE:
<223> OTHER INFORMATION: 29D9H8 heavy chain variable region

<400> SEQUENCE: 9

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
                20                  25                  30

Glu Met His Trp Val Lys Gln Thr Pro Val His Gly Leu Glu Trp Ile
            35                  40                  45

Gly Gly Ile Asp Pro Glu Thr Gly Gly Thr Ala Ser Asn Gln Lys Phe
        50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

```
Thr Ser Gly Asp Tyr Phe Gly Gly Pro Phe Ala Tyr Trp Gly Gln
            100                 105                 110
Gly Thr Leu Val Thr Val Ser Ala
        115                 120

<210> SEQ ID NO 10
<211> LENGTH: 5
<212> TYPE: PRT
<213> ORGANISM: Artificial sequence
<220> FEATURE:
<223> OTHER INFORMATION: 29D9H8 heavy chain CDR1

<400> SEQUENCE: 10

Asp Tyr Glu Met His
1               5

<210> SEQ ID NO 11
<211> LENGTH: 17
<212> TYPE: PRT
<213> ORGANISM: Artificial sequence
<220> FEATURE:
<223> OTHER INFORMATION: 29D9H8 heavy chain CDR2

<400> SEQUENCE: 11

Gly Ile Asp Pro Glu Thr Gly Gly Thr Ala Ser Asn Gln Lys Phe Lys
1               5                   10                  15

Gly

<210> SEQ ID NO 12
<211> LENGTH: 11
<212> TYPE: PRT
<213> ORGANISM: Artificial sequence
<220> FEATURE:
<223> OTHER INFORMATION: 29D9H8 heavy chain CDR3

<400> SEQUENCE: 12

Gly Asp Tyr Phe Gly Gly Gly Pro Phe Ala Tyr
1               5                   10

<210> SEQ ID NO 13
<211> LENGTH: 107
<212> TYPE: PRT
<213> ORGANISM: Artificial sequence
<220> FEATURE:
<223> OTHER INFORMATION: 29D9H8 light chain variable region

<400> SEQUENCE: 13

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Asp Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105
```

<210> SEQ ID NO 14
<211> LENGTH: 11
<212> TYPE: PRT
<213> ORGANISM: Artificial sequence
<220> FEATURE:
<223> OTHER INFORMATION: 29D9H8 light chain CDR1

<400> SEQUENCE: 14

Lys Ala Ser Gln Asp Ile Asn Ser Tyr Leu Ser
1               5                   10

<210> SEQ ID NO 15
<211> LENGTH: 7
<212> TYPE: PRT
<213> ORGANISM: Artificial sequence
<220> FEATURE:
<223> OTHER INFORMATION: 29D9H8 light chain CDR2

<400> SEQUENCE: 15

Arg Ala Asn Arg Leu Val Asp
1               5

<210> SEQ ID NO 16
<211> LENGTH: 9
<212> TYPE: PRT
<213> ORGANISM: Artificial sequence
<220> FEATURE:
<223> OTHER INFORMATION: 29D9H8 light chain CDR3

<400> SEQUENCE: 16

Leu Gln Tyr Asp Glu Phe Pro Tyr Thr
1               5

<210> SEQ ID NO 17
<211> LENGTH: 118
<212> TYPE: PRT
<213> ORGANISM: Artificial sequence
<220> FEATURE:
<223> OTHER INFORMATION: 28A2E11 heavy chain variable region

<400> SEQUENCE: 17

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

His Asp Lys Ala Thr Leu Thr Ala Asp Thr Ser Ser Asn Thr Ala Tyr
65                  70                  75                  80

Leu Gln Phe Ser Ser Leu Ala Ser Glu Asp Thr Ala Val Tyr Tyr Cys
                85                  90                  95

Thr Arg Tyr Asp Tyr Tyr Gly Pro Phe Ala Tyr Trp Gly Gln Gly Thr
            100                 105                 110

Leu Val Thr Val Ser Ala
        115

<210> SEQ ID NO 18
<211> LENGTH: 5
<212> TYPE: PRT
<213> ORGANISM: Artificial sequence
<220> FEATURE:
<223> OTHER INFORMATION: 28A2E11 heavy chain CDR1

```
<400> SEQUENCE: 18

Asp Tyr Tyr Met His
1               5

<210> SEQ ID NO 19
<211> LENGTH: 17
<212> TYPE: PRT
<213> ORGANISM: Artificial sequence
<220> FEATURE:
<223> OTHER INFORMATION: 28A2E11 heavy chain CDR2

<400> SEQUENCE: 19

Arg Ile Asp Pro Glu Asp Gly Glu Thr Lys Tyr Ala Pro Lys Phe His
1               5                   10                  15

Asp

<210> SEQ ID NO 20
<211> LENGTH: 9
<212> TYPE: PRT
<213> ORGANISM: Artificial sequence
<220> FEATURE:
<223> OTHER INFORMATION: 28A2E11 heavy chain CDR3

<400> SEQUENCE: 20

Tyr Asp Tyr Tyr Gly Pro Phe Ala Tyr
1               5

<210> SEQ ID NO 21
<211> LENGTH: 109
<212> TYPE: PRT
<213> ORGANISM: Artificial sequence
<220> FEATURE:
<223> OTHER INFORMATION: 28A2E11 light chain variable region

<400> SEQUENCE: 21

Gln Ala Val Val Thr Gln Glu Ser Val Leu Thr Thr Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Ile Gly Gly Thr Asn Asn Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ile Asn
                85                  90                  95

His Phe Ile Phe Gly Ser Gly Thr Lys Val Thr Val Leu
                100                 105

<210> SEQ ID NO 22
<211> LENGTH: 14
<212> TYPE: PRT
<213> ORGANISM: Artificial sequence
<220> FEATURE:
<223> OTHER INFORMATION: 28A2E11 light chain CDR1

<400> SEQUENCE: 22

Arg Ser Ser Thr Gly Ala Val Thr Thr Ser Asn Tyr Ala Asn
1               5                   10
```

```
<210> SEQ ID NO 23
<211> LENGTH: 7
<212> TYPE: PRT
<213> ORGANISM: Artificial sequence
<220> FEATURE:
<223> OTHER INFORMATION: 28A2E11 light chain CDR2

<400> SEQUENCE: 23

Gly Thr Asn Asn Arg Ala Pro
1               5

<210> SEQ ID NO 24
<211> LENGTH: 9
<212> TYPE: PRT
<213> ORGANISM: Artificial sequence
<220> FEATURE:
<223> OTHER INFORMATION: 28A2E11 light chain CDR3

<400> SEQUENCE: 24

Ala Leu Trp Tyr Ile Asn His Phe Ile
1               5

<210> SEQ ID NO 25
<211> LENGTH: 118
<212> TYPE: PRT
<213> ORGANISM: Artificial sequence
<220> FEATURE:
<223> OTHER INFORMATION: 35E2C3 heavy chain variable region

<400> SEQUENCE: 25

Glu Val Gln Leu Gln Glu Ser Gly Pro Gly Leu Ala Lys Pro Ser Gln
1               5                   10                  15

Thr Leu Ser Leu Thr Cys Ser Val Thr Gly Tyr Ser Ile Thr Ser Asp
            20                  25                  30

Tyr Trp Asn Trp Ile Arg Lys Phe Pro Gly Asn Lys Leu Glu Tyr Met
        35                  40                  45

Gly Tyr Ile Ser Tyr Asn Gly Asn Thr Tyr Tyr Asn Pro Ser Leu Lys
    50                  55                  60

Ser Gln Ile Ser Ile Thr Arg Asp Thr Ser Lys Asn Gln Leu Tyr Leu
65                  70                  75                  80

Gln Leu Lys Ser Ala Thr Thr Glu Asp Thr Ala Thr Tyr Tyr Cys Ala
                85                  90                  95

Arg Leu Ala Lys Trp Thr Trp Tyr Phe Asp Ile Trp Gly Thr Gly Thr
            100                 105                 110

Thr Val Thr Val Ser Ser
        115

<210> SEQ ID NO 26
<211> LENGTH: 5
<212> TYPE: PRT
<213> ORGANISM: Artificial sequence
<220> FEATURE:
<223> OTHER INFORMATION: 35E2C3 heavy chain CDR1

<400> SEQUENCE: 26

Ser Asp Tyr Trp Asn
1               5

<210> SEQ ID NO 27
<211> LENGTH: 16
<212> TYPE: PRT
<213> ORGANISM: Artificial sequence
<220> FEATURE:
<223> OTHER INFORMATION: 35E2C3 heavy chain CDR2
```

```
<400> SEQUENCE: 27

Tyr Ile Ser Tyr Asn Gly Asn Thr Tyr Tyr Asn Pro Ser Leu Lys Ser
1               5                   10                  15

<210> SEQ ID NO 28
<211> LENGTH: 10
<212> TYPE: PRT
<213> ORGANISM: Artificial sequence
<220> FEATURE:
<223> OTHER INFORMATION: 35E2C3 heavy chain CDR3

<400> SEQUENCE: 28

Leu Ala Lys Trp Thr Trp Tyr Phe Asp Ile
1               5                   10

<210> SEQ ID NO 29
<211> LENGTH: 107
<212> TYPE: PRT
<213> ORGANISM: Artificial sequence
<220> FEATURE:
<223> OTHER INFORMATION: 35E2C3 light chain variable region

<400> SEQUENCE: 29

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Ser Leu Pro Lys Leu Leu Ile
        35                  40                  45

Tyr Lys Ala Ser Asp Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gly Gly Thr Lys Leu Glu Ile Lys
            100                 105

<210> SEQ ID NO 30
<211> LENGTH: 11
<212> TYPE: PRT
<213> ORGANISM: Artificial sequence
<220> FEATURE:
<223> OTHER INFORMATION: 35E2C3 light chain CDR1

<400> SEQUENCE: 30

His Ala Ser Gln Asn Ile Asn Val Trp Leu Ser
1               5                   10

<210> SEQ ID NO 31
<211> LENGTH: 7
<212> TYPE: PRT
<213> ORGANISM: Artificial sequence
<220> FEATURE:
<223> OTHER INFORMATION: 35E2C3 light chain CDR2

<400> SEQUENCE: 31

Lys Ala Ser Asp Leu His Thr
1               5
```

```
<210> SEQ ID NO 32
<211> LENGTH: 9
<212> TYPE: PRT
<213> ORGANISM: Artificial sequence
<220> FEATURE:
<223> OTHER INFORMATION: 35E2C3 light chain CDR3

<400> SEQUENCE: 32

Gln Gln Gly Gln Ser Tyr Pro Tyr Thr
1               5

<210> SEQ ID NO 33
<211> LENGTH: 121
<212> TYPE: PRT
<213> ORGANISM: Artificial sequence
<220> FEATURE:
<223> OTHER INFORMATION: 70F10A10 heavy chain variable region

<400> SEQUENCE: 33

Gln Ile Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Asp Gly Gln Gly Leu Glu Trp Ile
        35                  40                  45

Gly Glu Ile Tyr Pro Arg Ser Gly Asn Thr Asp Tyr Asn Glu Lys Phe
    50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Ser Ser Phe Thr Thr Leu Val Pro Thr Asp Tyr Phe Asp Tyr Trp Gly
            100                 105                 110

Gln Gly Thr Thr Leu Thr Val Ser Ser
        115                 120

<210> SEQ ID NO 34
<211> LENGTH: 5
<212> TYPE: PRT
<213> ORGANISM: Artificial sequence
<220> FEATURE:
<223> OTHER INFORMATION: 70F10A10 heavy chain CDR1

<400> SEQUENCE: 34

Ser Tyr Gly Ile Ser
1               5

<210> SEQ ID NO 35
<211> LENGTH: 17
<212> TYPE: PRT
<213> ORGANISM: Artificial sequence
<220> FEATURE:
<223> OTHER INFORMATION: 70F10A10 heavy chain CDR2

<400> SEQUENCE: 35

Glu Ile Tyr Pro Arg Ser Gly Asn Thr Asp Tyr Asn Glu Lys Phe Lys
1               5                   10                  15

Gly

<210> SEQ ID NO 36
<211> LENGTH: 12
<212> TYPE: PRT
<213> ORGANISM: Artificial sequence
```

<220> FEATURE:
<223> OTHER INFORMATION: 70F10A10 heavy chain CDR3

<400> SEQUENCE: 36

Phe Thr Thr Leu Val Pro Thr Asp Tyr Phe Asp Tyr
1               5                   10

<210> SEQ ID NO 37
<211> LENGTH: 113
<212> TYPE: PRT
<213> ORGANISM: Artificial sequence
<220> FEATURE:
<223> OTHER INFORMATION: 70F10A10 light chain variable region

<400> SEQUENCE: 37

Asp Ile Met Met Ser Gln Ser Pro Ser Ser Leu Ala Val Ser Val Gly
1               5                   10                  15

Glu Lys Val Ser Met Thr Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Met Leu Ile Tyr Trp Ala Ser Thr Arg Glu Thr Gly Val
    50                  55                  60

Pro Asp Arg Phe Thr Gly Ser Gly Ser Gly Thr Asp Phe Thr Leu Thr
65                  70                  75                  80

Ile Ser Ser Val Met Ala Glu Asp Leu Ala Val Tyr Tyr Cys His Gln
                85                  90                  95

Tyr Phe Thr Tyr Pro Arg Thr Phe Gly Asp Gly Thr Lys Leu Glu Val
            100                 105                 110

Lys

<210> SEQ ID NO 38
<211> LENGTH: 17
<212> TYPE: PRT
<213> ORGANISM: Artificial sequence
<220> FEATURE:
<223> OTHER INFORMATION: 70F10A10 light chain CDR1

<400> SEQUENCE: 38

Lys Ser Ser Gln Ser Leu Leu Tyr Ser Ser Asn Gln Lys Asn Tyr Leu
1               5                   10                  15

Ala

<210> SEQ ID NO 39
<211> LENGTH: 7
<212> TYPE: PRT
<213> ORGANISM: Artificial sequence
<220> FEATURE:
<223> OTHER INFORMATION: 70F10A10 light chain CDR2

<400> SEQUENCE: 39

Trp Ala Ser Thr Arg Glu Thr
1               5

<210> SEQ ID NO 40
<211> LENGTH: 9
<212> TYPE: PRT
<213> ORGANISM: Artificial sequence
<220> FEATURE:
<223> OTHER INFORMATION: 70F10A10 light chain CDR3

```
<400> SEQUENCE: 40

His Gln Tyr Phe Thr Tyr Pro Arg Thr
1               5

<210> SEQ ID NO 41
<211> LENGTH: 123
<212> TYPE: PRT
<213> ORGANISM: Artificial sequence
<220> FEATURE:
<223> OTHER INFORMATION: 35H6E1 heavy chain variable region

<400> SEQUENCE: 41

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
            20                  25                  30

Asn Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Glu Ser Arg Leu Thr Ile Ser Lys Asp Thr Ser Arg Asn Gln Val
65                  70                  75                  80

Phe Leu Lys Ile Thr Ser Val Asp Thr Ala Asp Ser Ala Thr Tyr Tyr
                85                  90                  95

Cys Ala Arg Arg Thr Asn Tyr Phe Ser Thr Arg Asp Tyr Phe Asp Tyr
            100                 105                 110

Trp Gly Gln Gly Thr Thr Leu Thr Val Ser Ser
        115                 120

<210> SEQ ID NO 42
<211> LENGTH: 7
<212> TYPE: PRT
<213> ORGANISM: Artificial sequence
<220> FEATURE:
<223> OTHER INFORMATION: 35H6E1 heavy chain CDR1

<400> SEQUENCE: 42

Thr Ser Asn Met Gly Val Ser
1               5

<210> SEQ ID NO 43
<211> LENGTH: 16
<212> TYPE: PRT
<213> ORGANISM: Artificial sequence
<220> FEATURE:
<223> OTHER INFORMATION: 35H6E1 heavy chain CDR2

<400> SEQUENCE: 43

His Ile Tyr Trp Asp Asp Asp Lys Arg Tyr Asn Pro Ser Leu Glu Ser
1               5                   10                  15

<210> SEQ ID NO 44
<211> LENGTH: 13
<212> TYPE: PRT
<213> ORGANISM: Artificial sequence
<220> FEATURE:
<223> OTHER INFORMATION: 35H6E1 heavy chain CDR3

<400> SEQUENCE: 44

Arg Thr Asn Tyr Phe Ser Thr Arg Asp Tyr Phe Asp Tyr
1               5                   10
```

```
<210> SEQ ID NO 45
<211> LENGTH: 107
<212> TYPE: PRT
<213> ORGANISM: Artificial sequence
<220> FEATURE:
<223> OTHER INFORMATION: 35H6E1 light chain variable region

<400> SEQUENCE: 45

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Val Trp Tyr Gln Gln Lys Gln Gly Lys Ser Pro Gln Leu Leu Val
        35                  40                  45

Tyr Ala Ala Thr Lys Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Phe Pro Trp
                85                  90                  95

Thr Phe Gly Gly Gly Thr Lys Leu Glu Ile Lys
            100                 105

<210> SEQ ID NO 46
<211> LENGTH: 11
<212> TYPE: PRT
<213> ORGANISM: Artificial sequence
<220> FEATURE:
<223> OTHER INFORMATION: 35H6E1 light chain CDR1

<400> SEQUENCE: 46

Arg Ala Ser Glu Asn Ile Tyr Ser Asn Leu Val
1               5                   10

<210> SEQ ID NO 47
<211> LENGTH: 7
<212> TYPE: PRT
<213> ORGANISM: Artificial sequence
<220> FEATURE:
<223> OTHER INFORMATION: 35H6E1 light chain CDR2

<400> SEQUENCE: 47

Ala Ala Thr Lys Leu Ala Asp
1               5

<210> SEQ ID NO 48
<211> LENGTH: 9
<212> TYPE: PRT
<213> ORGANISM: Artificial sequence
<220> FEATURE:
<223> OTHER INFORMATION: 35H6E1 light chain CDR3

<400> SEQUENCE: 48

Gln His Phe Trp Gly Phe Pro Trp Thr
1               5

<210> SEQ ID NO 49
<211> LENGTH: 381
<212> TYPE: DNA
<213> ORGANISM: Artificial sequence
<220> FEATURE:
<223> OTHER INFORMATION: P4_4H12 heavy chain variable region
```

-continued

```
<400> SEQUENCE: 49
gaggtgcagc tggtggagac cggggggaggc gtggtccagc ctggagggtc cctgagactc    60
tcctgtgcag cctctggatt caccttcagt agctatgcta tgcactgggt ccgccaggct    120
ccaggcaagg ggctggagtg ggtggcagtt atatcatatg atggaagcaa taaatactac    180
gcagactccg tgaagggccg attcaccatc tccagagaca attccaagaa cacgctgtat    240
ctgcaaatga acagcctgag agctgaggac acggctgtgt attactgtgc gagagatccg    300
gtaggatatt gtagtggtgg tagctgctac tactacggta tggacgtctg gggccaaggg    360
accacggtca ccgtctcctc a                                              381

<210> SEQ ID NO 50
<211> LENGTH: 324
<212> TYPE: DNA
<213> ORGANISM: Artificial sequence
<220> FEATURE:
<223> OTHER INFORMATION: P4_4H12 light chain variable region

<400> SEQUENCE: 50
gaaattgtga tgacgcagtc tccagccacc ctgtctttgt ctccagggga aagagccacc    60
ctctcctgca gggccagtca gagtgttagc agcagctact tagcctggta ccagcagaaa    120
cctggccagg ctcccaggct cctcatctat ggtgcatcca cagggccac tggcataccg     180 gacaggttct atggcagtgg gtctgggaca gacttcactc tcaccatcag caggctggag    240
cctgaggatt ttgcagtgta ttattgtcag caatatggta gctcacctac gacgttcggc    300
ctagggacca aggtggtaat caaa                                           324

<210> SEQ ID NO 51
<211> LENGTH: 360
<212> TYPE: DNA
<213> ORGANISM: Artificial sequence
<220> FEATURE:
<223> OTHER INFORMATION: 29D9H8 heavy chain variable region

<400> SEQUENCE: 51
caggttcaac tacagcagtc tggggctgag ctggtgaggc ctggggcttc agtgacgctg    60
tcctgcaagg cttcgggcta cacatttact gactatgaaa tgcactgggt gaagcagaca    120
cctgtgcatg gcctggaatg gattggaggt attgatcctg aaactggtgg cactgcctcc    180
aatcagaagt tcaagggcaa ggccatactg actgcagaca atcctccag cacagcctac    240 atggagctcc gcagcctgac atctgaggac tctgccgtct attactgtac aagtggggat    300
tacttcggtg gtggccctt tgcttactgg ggccaaggga ctctggtcac tgtctctgca    360

<210> SEQ ID NO 52
<211> LENGTH: 321
<212> TYPE: DNA
<213> ORGANISM: Artificial sequence
<220> FEATURE:
<223> OTHER INFORMATION: 29D9H8 light chain variable region

<400> SEQUENCE: 52
gacatcaaga tgacccagtc tccatcttcc atgtatgcat ctctaggaga gagagtcact    60
atcacttgca aggcgagtca ggacattaat agctatttaa gctggttcca gcagaaacca    120
gggaaatctc ctaagaccct gatctatcgt gcaaacagat tggtagatgg ggtcccatca    180
aggttcagtg gcagtggatc tgggcaagat tattctctca ccatcagcag cctggattat    240
```

```
gaagatatgg gaatttatta ttgtctacag tatgatgagt ttccgtacac gttcggaggg    300
gggaccaagc tggaaataaa a                                              321
```

<210> SEQ ID NO 53
<211> LENGTH: 354
<212> TYPE: DNA
<213> ORGANISM: Artificial sequence
<220> FEATURE:
<223> OTHER INFORMATION: 28A2E11 heavy chain variable region

<400> SEQUENCE: 53

```
gaggttcagc tgcagcagtc tggggcagag cttgtgaagc cgggggcctc agtcaagttg    60
tcctgcacag cttctggctt caacattaaa gactactata tgcactgggt gaagcagagg   120
actgaacagg gcctggagtg gattggaagg attgatcctg aggatggtga aactaaatat   180
gccccgaaat tccacgacaa ggccacttta acagcagaca catcctccaa cacagcctac   240
ctgcagttca gcagcctggc atctgaggac actgccgtct attactgtac tagatacgat   300
tactacggtc cttttgctta ctggggccaa gggactctgg tcactgtctc tgca         354
```

<210> SEQ ID NO 54
<211> LENGTH: 327
<212> TYPE: DNA
<213> ORGANISM: Artificial sequence
<220> FEATURE:
<223> OTHER INFORMATION: 28A2E11 light chain variable region

<400> SEQUENCE: 54

```
caagctgttg tgactcagga atctgtactc accacatcac ctggtgaaac agtcacactc    60
acttgtcgct caagtactgg ggctgttaca actagtaact atgccaactg gtccaagaa    120 aaaccagatc atttattcac tggtctaata ggtggtacca caaccgagc tccaggtgtt   180 cctgccagat tctcaggctc cctgattgga gacaaggctg ccctcaccat cacaggggca   240
cagactgagg atgaggcaat atatttctgt gctctatggt acatcaacca ttttattttc   300
ggcagtggaa ccaaggtcac tgtccta                                        327
```

<210> SEQ ID NO 55
<211> LENGTH: 354
<212> TYPE: DNA
<213> ORGANISM: Artificial sequence
<220> FEATURE:
<223> OTHER INFORMATION: 35E2C3 heavy chain variable region

<400> SEQUENCE: 55

```
gaggtgcagc ttcaggagtc aggacctggc ctggcaaaac cttctcagac tctgtccctc    60
acctgttctg tcactggcta ctccatcacc agtgattact ggaactggat ccggaagttc   120
ccagggaata acttgagta catgggggtat ataagttaca atggtaacac ttactacaat   180
ccatctctca aaagtcaaat ctccataact cgagacactt ccaagaacca actttacctg   240
cagttgaaat ctgcgacgac tgaggacaca gccacatatt actgtgcaag acttgctaag   300
tggacctggt acttcgatat ctggggcaca gggaccacgg tcaccgtctc ctca         354
```

<210> SEQ ID NO 56
<211> LENGTH: 321
<212> TYPE: DNA
<213> ORGANISM: Artificial sequence
<220> FEATURE:
<223> OTHER INFORMATION: 35E2C3 light chain variable region

<400> SEQUENCE: 56

```
gacatccaga tgaaccagtc tccatccagt ctgtctgcat cccttggaga cacaattacc        60
attacttgcc atgccagtca gaacattaat gtttggttaa gctggtacca gcagaaacca       120
ggaagtcttc ctaagctatt gatctataag gcttccgact tgcacacagg cgtcccatca       180
aggtttagtg gcagtggatc tggaacaggt ttcacattaa ccatcagcag cctgcagcct       240
gaagacattg ccacttacta ctgtcaacag ggtcaaagtt atccatacac gttcggaggg       300
gggaccaagc tggaaataaa a                                                  321
```

<210> SEQ ID NO 57
<211> LENGTH: 363
<212> TYPE: DNA
<213> ORGANISM: Artificial sequence
<220> FEATURE:
<223> OTHER INFORMATION: 70F10A10 heavy chain variable region

<400> SEQUENCE: 57

```
cagatccagc tgcagcagtc tggagctgaa ctggcgaggc ctggggcttc agtgaagctg        60
tcctgcaagg cttctggcta cacattcaca agttatggta taagctgggt gaagcagaga       120
gatggacagg gccttgagtg gattggagag atttatccta gaagtggtaa tactgactac       180
aatgagaagt tcaagggcaa ggccacactg actgcagaca atcctccag cacagcgtac        240
atggagctcc gcagtctgac atctgaggac tctgcggtct acttctgttc aagttttact       300
acgctggttc caacggacta ctttgactac tggggccaag gcaccactct cacagtctcc       360
tca                                                                      363
```

<210> SEQ ID NO 58
<211> LENGTH: 339
<212> TYPE: DNA
<213> ORGANISM: Artificial sequence
<220> FEATURE:
<223> OTHER INFORMATION: 70F10A10 light chain variable region

<400> SEQUENCE: 58

```
gacattatga tgtcacagtc tccatcctcc ctagctgtgt cagttggaga gaaggttagt        60
atgacctgca gtccagtca gagcctttta tatagtagca tcaaaagaa ttatttggcc        120
tggtaccagc agaaaccagg gcagtctcct aaaaatgctga tttactgggc atccactagg      180
gaaactgggg tccctgatcg cttcacaggc agtggatctg gacagatttt cactctcacc      240
atcagcagtg tgatggctga agacctggca gtttattact gtcaccaata ttttacctat      300
cctcggacgt tcggtgacgg caccaagttg gaagtcaaa                               339
```

<210> SEQ ID NO 59
<211> LENGTH: 369
<212> TYPE: DNA
<213> ORGANISM: Artificial sequence
<220> FEATURE:
<223> OTHER INFORMATION: 35H6E1 heavy chain variable region

<400> SEQUENCE: 59

```
caggttactc tgaaagagtc tggccctggg attttgcagt cctcccagac cctcagtctg        60
acttgttctt tttctgggtt ttcactgagc acttctaata tgggtgtgag ctggattcgt       120
cagccttcag aaagggtct ggagtggctg gcacacattt attgggatga tgacaagcgc        180
tataacccat ccctggagag ccggctcaca atctccaagg atacctccag aaaccaggtt      240
ttcctcaaga tcaccagtgt agacactgca gattctgcca catactactg cgctcgaaga      300
```

```
actaattact tcagtactag ggactatttt gactactggg gccaaggcac cactctcaca      360
gtctcctca                                                              369
```

<210> SEQ ID NO 60
<211> LENGTH: 321
<212> TYPE: DNA
<213> ORGANISM: Artificial sequence
<220> FEATURE:
<223> OTHER INFORMATION: 35H6E1 light chain variable region

<400> SEQUENCE: 60

```
gacatccaga tgacgcagtc tccagcctcc ctatctgtgt ctgtgggaga aactgtcacc       60
atcacatgtc gagcaagtga gaatatttac agtaatttag tttggtatca gcagaaacag      120
gggaaatctc ctcaactcct ggtctatgct gcaacaaagt tagcagatgg tgtgccatca      180
aggttcagtg gcagtggatc aggcacacaa tattccctca agatcaacag cctgcagtct      240
gaagattttg ggagttatta ctgtcaacat tttgggggtt ttccgtggac gttcggtgga      300
ggcaccaagc tggaaatcaa a                                                321
```

<210> SEQ ID NO 61
<211> LENGTH: 414
<212> TYPE: DNA
<213> ORGANISM: Homo sapiens

<400> SEQUENCE: 61

```
atggcgcttt tgttgaccac ggtcattgct ctcacttgcc ttggcggctt tgcctcccca       60
ggccctgtgc ctccctctac agccctcagg gagctcattg aggagctggt caacatcacc      120
cagaaccaga aggctccgct ctgcaatggc agcatggtat ggagcatcaa cctgacagct      180
ggcatgtact gtgcagccct ggaatccctg atcaacgtgt caggctgcag tgccatcgag      240
aagacccaga ggatgctgag cggattctgc ccgcacaagg tctcagctgg gcagttttcc      300
agcttgcatg tccgagacac caaaatcgag gtggcccagt ttgtaaagga cctgctctta      360
catttaaaga aacttttttcg cgagggacgg ttcaaccatc atcaccatca ccat           414
```

<210> SEQ ID NO 62
<211> LENGTH: 414
<212> TYPE: DNA
<213> ORGANISM: Homo sapiens

<400> SEQUENCE: 62

```
atggcgcttt tgttgaccac ggtcattgct ctcacttgcc ttggcggctt tgcctcccca       60
ggccctgtgc ctccctctac agccctcagg gagctcattg aggagctggt caacatcacc      120
cagaaccaga aggctccgct ctgcaatggc agcatggtat ggagcatcaa cctgacagct      180
ggcatgtact gtgcagccct ggaatccctg atcaacgtgt caggctgcag tgccatcgag      240
aagacccaga ggatgctgag cggattctgc ccgcacaagg tctcagctgg gcagttttcc      300
agcttgcatg tccgagacac caaaatcgag gtggcccagt ttgtaaagga cctgctctta      360
catttaaaga aacttttttcg cgagggacag ttcaaccatc atcaccatca ccat           414
```

<210> SEQ ID NO 63
<211> LENGTH: 1284
<212> TYPE: DNA
<213> ORGANISM: Homo sapiens

<400> SEQUENCE: 63

```
atggagtggc cggcgcggct ctgcgggctg tgggcgctgc tgctctgcgc cggcggcggg      60
ggcggggggcg ggggcgccgc gcctacggaa actcagccac ctgtgacaaa tttgagtgtc    120
tctgttgaaa acctctgcac agtaatatgg acatggaatc cacccgaggg agccagctca    180
aattgtagtc tatggtattt tagtcatttt ggcgacaaac aagataagaa atagctccg     240
gaaactcgtc gttcaataga agtacccctg aatgagagga tttgtctgca agtgggtcc     300
cagtgtagca ccaatgagag tgagaagcct agcattttgg ttgaaaaatg catctcaccc    360
ccagaaggtg atcctgagtc tgctgtgact gagcttcaat gcatttggca caacctgagc    420
tacatgaagt gttcttggct ccctggaagg aataccagtc ccgacactaa ctatactctc    480
tactattggc acagaagcct ggaaaaaatt catcaatgtg aaaacatctt tagagaaggc    540
caatactttg gttgttcctt tgatctgacc aaagtgaagg attccagttt tgaacaacac    600
agtgtccaaa taatggtcaa ggataatgca ggaaaaatta aaccatcctt caatatagtg    660
cctttaactt cccgtgtgaa acctgatcct ccacatatta aaaacctctc cttccacaat    720
gatgacctat atgtgcaatg ggagaatcca cagaatttta ttagcagatg cctattttat    780
gaagtagaag tcaataacag ccaaactgag acacataatg ttttctacgt ccaagaggct    840
aaatgtgaga atccagaatt tgagagaaat gtggagaata catcttgttt catggtccct    900
ggtgttcttc ctgatacttt gaacacagtc agaataagag tcaaaacaaa taagttatgc    960
tatgaggatg acaaactctg gagtaattgg agccaagaaa tgagtatagg taagaagcgc   1020
aattccacac tctacataac catgttactc attgttccag tcatcgtcgc aggtgcaatc   1080
atagtactcc tgctttacct aaaaaggctc aagattatta tattccctcc aattcctgat   1140
cctggcaaga ttttaaaga atgtttggga gaccagaatg atgatactct gcactggaag   1200
aagtacgaca tctatgagaa gcaaaccaag gaggaaaccg actctgtagt gctgatagaa   1260
aacctgaaga agcctctca gtga                                          1284
```

<210> SEQ ID NO 64
<211> LENGTH: 1143
<212> TYPE: DNA
<213> ORGANISM: Homo sapiens

<400> SEQUENCE: 64

```
atggctttcg tttgcttggc tatcggatgc ttatatacct ttctgataag cacaacattt      60
ggctgtactt catcttcaga caccgagata aaagttaacc ctcctcagga ttttgagata    120
gtggatcccg gatacttagg ttatctctat ttgcaatggc aacccccact gtctctggat    180
cattttaagg aatgcacagt ggaatatgaa ctaaaatacc gaaacattgg tagtgaaaca    240
tggaagacca tcattaccaa gaatctacat acaaagatg ggtttgatct taacaagggc    300
attgaagcga agatacacac gcttttacca tggcaatgca caaatggatc agaagttcaa    360
agttcctggg cagaaactac ttattggata tcaccacaag gaattccaga actaaagtt     420
caggatatgg attgcgtata ttacaattgg caatatttac tctgttcttg gaaacctggc    480
ataggtgtac ttcttgatac caattacaac ttgttttact ggtatgaggg cttggatcat    540
gcattacagt gtgttgatta catcaaggct gatggacaaa atataggatg cagatttccc    600
tatttggagg catcagacta taagattttc tatatttgtg ttaatggatc atcagagaac    660
aagcctatca gatccagtta tttcactttt cagcttcaaa atatagttaa accttttgccg    720
ccagtctatc ttacttttac tcgggagagt tcatgtgaaa ttaagctgaa atggagcata    780
```

| | |
|---|---|
| cctttgggac ctattccagc aaggtgtttt gattatgaaa ttgagatcag agaagatgat | 840 |
| actaccttgg tgactgctac agttgaaaat gaaacataca ccttgaaaac aacaaatgaa | 900 |
| acccgacaat tatgctttgt agtaagaagc aaagtgaata tttattgctc agatgacgga | 960 |
| atttggagtg agtggagtga taaacaatgc tgggaaggtg aagacctatc gaagaaaact | 1020 |
| ttgctacgtt tctggctacc atttggtttc atcttaatat tagttatatt tgtaaccggt | 1080 |
| ctgcttttgc gtaagccaaa cacctaccca aaaatgattc cagaattttt ctgtgataca | 1140 |
| tga | 1143 |

<210> SEQ ID NO 65
<211> LENGTH: 2478
<212> TYPE: DNA
<213> ORGANISM: Homo sapiens

<400> SEQUENCE: 65

| | |
|---|---|
| atggggtggc tttgctctgg gctcctgttc cctgtgagct gcctggtcct gctgcaggtg | 60 |
| gcaagctctg ggaacatgaa ggtcttgcag gagcccacct gcgtctccga ctacatgagc | 120 |
| atctctactt gcgagtggaa gatgaatggt cccaccaatt gcagcaccga gctccgcctg | 180 |
| ttgtaccagc tggttttttct gctctccgaa gcccacacgt gtatccctga gaacaacgga | 240 |
| ggcgcggggt gcgtgtgcca cctgctcatg gatgacgtgg tcagtgcgga taactataca | 300 |
| ctggacctgt gggctgggca gcagctgctg tggaagggcc cttcaagcc cagcgagcat | 360 |
| gtgaaaccca gggccccagg aaacctgaca gttcacacca atgtctccga cactctgctg | 420 |
| ctgacctgga gcaacccgta tccccctgac aattacctgt ataatcatct cacctatgca | 480 |
| gtcaacattt ggagtgaaaa cgacccggca gatttcagaa tctataacgt gacctaccta | 540 |
| gaaccctccc tccgcatcgc agccagcacc ctgaagtctg ggatttccta cagggcacgg | 600 |
| gtgagggcct gggctcagtg ctataacacc acctggagtg agtggagccc cagcaccaag | 660 |
| tggcacaact cctacaggga gcccttcgag cagcacctcc tgctgggcgt cagcgttttcc | 720 |
| tgcattgtca tcctggccgt ctgcctgttg tgctatgtca gcatcaccaa gattaagaaa | 780 |
| gaatggtggg atcagattcc caacccagcc cgcagccgcc tcgtggctat aataatccag | 840 |
| gatgctcagg ggtcacagtg ggagaagcgg tcccgaggcc aggaaccagc caagtgccca | 900 |
| cactggaaga attgtcttac caagctcttg ccctgttttc tggagcacaa catgaaaagg | 960 |
| gatgaagatc ctcacaaggc tgccaaagag atgccttttcc agggctctgg aaaatcagca | 1020 |
| tggtgcccag tggagatcag caagacagtc tctggccag agagcatcag cgtggtgcga | 1080 |
| tgtgtggagt tgtttgaggc cccggtggag tgtgaggagg aggaggaggt agaggaagaa | 1140 |
| aaagggagct tctgtgcatc gcctgagagc agcaggatg acttccagga gggaagggag | 1200 |
| ggcattgtgg cccggctaac agagagcctg ttcctggacc tgctcggaga ggagaatggg | 1260 |
| ggcttttgcc agcaggacat gggggagtca tgccttcttc caccttcggg aagtacgagt | 1320 |
| gctcacatgc cctgggatga gttcccaagt gcagggccca aggaggcacc tcctgggc | 1380 |
| aaggagcagc ctctccacct ggagccaagt cctcctgcca gcccgaccca gagtccagac | 1440 |
| aacctgactt gcacagagac gcccctcgtc atcgcaggca accctgctta ccgcagcttc | 1500 |
| agcaactccc tgagccagtc accgtgtccc agagagctgg tccagaccc actgctggcc | 1560 |
| agacacctgg aggaagtaga acccgagatg ccctgtgtcc cccagctctc tgagccaacc | 1620 |
| actgtgccca accctgagcc agaaacctgg gagcagatct tccgccgaaa tgtcctccag | 1680 |
| catggggcag ctgcagcccc cgtctcggcc cccaccagtg gctatcagga gtttgtacat | 1740 |

```
gcggtggagc agggtggcac ccaggccagt gcggtggtgg gcttgggtcc cccaggagag    1800
gctggttaca aggccttctc aagcctgctt gccagcagtg ctgtgtcccc agagaaatgt    1860
gggtttgggg ctagcagtgg ggaagagggg tataagcctt tccaagacct cattcctggc    1920
tgccctgggg accctgcccc agtccctgtc cccttgttca cctttggact ggacagggag    1980
ccacctcgca gtccgcagag ctcacatctc ccaagcagct ccccagagca cctgggtctg    2040
gagccggggg aaaaggtaga ggacatgcca aagcccccac ttccccagga gcaggccaca    2100
gacccccttg tggacagcct gggcagtggc attgtctact cagcccttac ctgccacctg    2160
tgcggccacc tgaaacagtg tcatggccag gaggatggtg gccagacccc tgtcatggcc    2220
agtccttgct gtggctgctg ctgtggagac aggtcctcgc cccctacaac cccctgagg    2280 gccccagacc cctctccagg tggggttcca ctggaggcca gtctgtgtcc ggcctccctg    2340
gcaccctcgg gcatctcaga gaagagtaaa tcctcatcat ccttccatcc tgccctggc    2400 aatgctcaga gctcaagcca gacccccaaa atcgtgaact ttgtctccgt gggacccaca    2460
tacatgaggg tctcttag                                                 2478
```

IL-13 ANTIBODY AND PREPARATION METHOD AND USE THEREOF

This application claims priority of Chinese Patent Application No. 201610333020.X filed on May 18, 2016 and Chinese Patent Application No. 201610474103.0 filed on Jun. 14, 2016. The entire content of the aforementioned application is hereby incorporated by reference.

FIELD OF INVENTION

The present invention relates to the antibody, and more specifically, relates to IL-13 antibody, method of its preparation and use thereof.

PRIOR ARTS

Bronchial asthma (asthma for short) is a common chronic airway inflammatory disease. It is usually accompanied by increased airway responsiveness, and recurrent symptoms such as wheezing, shortness of breath, chest tightness and/or coughing. Since the 1970s, asthma has become widespread. By 2011, around 235 million to 300 million people were affected worldwide, and about 250,000 people lost their lives. Clinically, asthma is usually treated by inhaling glucocorticoids such as steroids and assisting long-acting beta-adrenergic receptor agonists. However, about 10% of patients cannot be relieved by conventional airway inhalation. These patients usually need oral steroid drugs with serious side effects to control the condition, which are still accompanied by high mortality. Not only is the quality of life of patients greatly affected, but the direct medical costs and indirect costs result in huge individual and the socioeconomic burdens.

In recent years, with the in-depth study of asthma, it has been found that excessive release of soluble cytokines by Th2 cells induces IgE production in most asthma patients, resulting in increased degranulation of mast cells and eosinophils, thereby inducing airway allergic reactions and chronic airway inflammation involving various inflammatory cells. Among these cytokines, interleukin 13 (hereinafter referred to as IL-13) and interleukin 4 (hereinafter referred to as IL-4) play a very important role in this abovementioned process. IL-13 is a pleiotropic cytokine secreted mainly by Th2 cells, with a molecular weight of about 10 KDa. Its gene is located on chromosome 5 and closely linked to the IL-4 gene. IL-4 and IL-13, which are produced by Th2 cells, share the same receptor chain and have many similarities in function. In recent years, several animal experiments have confirmed that both IL-4 and IL-13 can cause an increase in airway responsiveness, eosinophil infiltration and mucus secretion. The increase in plasma IgE levels prevalent in asthmatic patients have also been confirmed to be the result of B cell proliferation and differentiation stimulated by IL-13. Recently, with the in-depth study of the single nucleotide polymorphism of IL-13 gene, a natural variant R130Q of IL-13 has also been found. Approximately, 25% of the chromosomes in the population are encoded with this variant, but the population can be increased to approximately 50% in asthma patients. Reports in the literature indicated that R130Q variant is directly related to the onset of asthma and are more prone to allergic symptoms. In-depth studies have found that patients expressing IL-13 variant R130Q have higher levels of IL-13 with stronger effect, follow by a greater risk of suffering from symptoms such as asthma (see May and Fung 2015, Cytokine 75:89).

The traditional hybridoma preparation technique, established 40 years ago by Kohler and Milstein (Kohler and Milstein 1975, Nature 256: 495), has now been widely used in the preparation and production of many monoclonal antibodies related to scientific research, diagnostics and therapy. Although the basic methods have been used so far, there are changes, improvements and innovations in many aspects, including the use of different strains of animals such as transgenic animals, the introduction of electrofusion technology, and the application of high-efficiency screening technology equipment such as ClonePix equipment, etc. Thereby the application of hybridoma technology is more diversified and efficient. The monoclonal antibody prepared by a conventional animal, such as mouse, can clone the gene of heavy chain variable region and light chain variable region of antibody by a conventional molecular biological method, and the variable region gene can be grafted to a human antibody constant region gene to form a human-mouse chimeric antibody (see U.S. Pat. No. 4,816,567) to greatly reducing immunogenicity when used in human. In addition, the CDR domain of the mouse antibody variable region can be grafted onto the human antibody framework, thereby reducing the component of mouse antibody to less than 5%, greatly increasing the safety of the antibody use in humans. The antibody obtained in this way is called a humanized antibody and is currently the main product in the drug market of antibody (see U.S. Pat. No. 5,225,539, et al).

The earliest appearance of phage display technology was in 1985, when Smith G P [see Smith G P 1985, Science 228 (4705): 1315-7] inserted a foreign gene into the gene III of the filamentous phage f1 for the first time to display the polypeptide encoded by the gene of interest on the surface of the phage as a fusion protein, thus inventing phage display technology. In the same year, a patent published by George Pieczenik (see U.S. Pat. No. 58,663,635, et al) describes a method for establishing a peptide library using phage display technology. After years of improvement and development, this technology has become a powerful tool for discovering new functional peptides and altering the properties of existing peptides.

Therefore, there is an urgent need for drugs that inhibit IL-13, such as IL-13 antibodies, for the prevention or treatment of bronchial asthma.

Content of the Present Invention

The technical problem to be solved herein is to provide an IL-13 antibody with high affinity and strong specificity, and preparation method and use thereof for overcoming the deficiency of lacking IL-13 antibody in the prior art. Having a high affinity, the IL-13 antibody can significantly inhibit the secretion of thymus and activation-regulated chemokine and periostin, as well as the expression of vascular cell adhesion molecule-1 and mouse airway hyperresponsiveness induced by IL-13. Therefore, it can be used in the preparation of a medicament for preventing or treating diseases such as bronchial asthma.

Recombinant human IL-13 protein was used as an immunogen in the present invention, and conventional hybridoma preparation techniques (see Kohler and Milstein, Nature, 1975, 256: 495) or phage display technology is adopted to obtain the lead antibody of IL-13 through a series of adjustments and improvements. Through the preliminary production, purification and identification of the lead antibody, the IL-13 antibody with high affinity to proteins such as human IL-13 protein was obtained. Subsequently, the amino acid sequences of the heavy chain variable region and the light chain variable region of the resulting IL-13 antibody were obtained by using sequencing of molecular biological methods, and a murine-human chimeric antibody molecule or a human antibody molecule was obtained.

The present invention provides an isolated protein, which comprises: one or more of heavy chain CDR1, heavy chain CDR2 and heavy chain CDR3 of the IL-13 antibody, and/or one or more of light chain CDR1, light chain CDR2, and light chain CDR3 of the IL-13 antibody, wherein the heavy chain CDR1 comprises the amino acid sequences of SEQ ID No.2, SEQ ID No.10, SEQ ID No.18, SEQ ID No.26, SEQ ID No.34 or SEQ ID No.42;

the heavy chain CDR2 comprises the amino acid sequences of SEQ ID No.3, SEQ ID No.11, SEQ ID No.19, SEQ ID No.27, SEQ ID No.35 or SEQ ID No.43;

the heavy chain CDR3 comprises the amino acid sequences of SEQ ID No.4, SEQ ID No.12, SEQ ID No.20, SEQ ID No.28, SEQ ID No.36 or SEQ ID No.44;

the light chain CDR1 comprises the amino acid sequences of SEQ ID No.6, SEQ ID No.14, SEQ ID No.22, SEQ ID No.30, SEQ ID No.38 or SEQ ID No.46;

the light chain CDR2 comprises the amino acid sequences of SEQ ID No.7, SEQ ID No.15, SEQ ID No.23, SEQ ID No.31, SEQ ID No.39 or SEQ ID No.47;

the light chain CDR3 comprises the amino acid sequences of SEQ ID No.8, SEQ ID No.16, SEQ ID No.24, SEQ ID No.32, SEQ ID No.40 or SEQ ID No.48;

Or, the amino acid sequences of the heavy chain CDR1 are at least 80% identical to the amino acid sequences of SEQ ID No.2, SEQ ID No.10, SEQ ID No.18, SEQ ID No.26, SEQ ID No.34 or SEQ ID No.42;

the amino acid sequences of the heavy chain CDR2 are at least 80% identical to the amino acid sequences of SEQ ID No.3, SEQ ID No.11, SEQ ID No.19, SEQ ID No.27, SEQ ID No.35 or SEQ ID No.43;

the amino acid sequences of the heavy chain CDR3 are at least 80% identical to the amino acid sequences of SEQ ID No.4, SEQ ID No.12, SEQ ID No.20, SEQ ID No.28, SEQ ID No.36 or SEQ ID No.44;

the amino acid sequences of the light chain CDR1 are at least 80% identical to the amino acid sequences of SEQ ID No.6, SEQ ID No.14, SEQ ID No.22, SEQ ID No.30, SEQ ID No.38 or SEQ ID No.46;

the amino acid sequences of the light chain CDR2 are at least 80% identical to the amino acid sequences of SEQ ID No.7, SEQ ID No.15, SEQ ID No.23, SEQ ID No.31, SEQ ID No.39 or SEQ ID No.47;

the amino acid sequences of the light chain CDR3 are at least 80% identical to the amino acid sequences of SEQ ID No.8, SEQ ID No.16, SEQ ID No.24, SEQ ID No.32, SEQ ID No.40 or SEQ ID No.48.

Preferably, the heavy chain CDR1 comprises the amino acid sequence of SEQ ID No.2, the heavy chain CDR2 comprises the amino acid sequence of SEQ ID No.3 and the heavy chain CDR3 comprises the amino acid sequence of SEQ ID No.4; the heavy chain heavy chain CDR1 comprises the amino acid sequence of SEQ ID No.10, the heavy chain CDR2 comprises the amino acid sequence of SEQ ID No.11 and the heavy chain CDR3 comprises the amino acid sequence of SEQ ID No.12; the heavy chain CDR1 comprises the amino acid sequence of SEQ ID No.18, the heavy chain CDR2 comprises the amino acid sequence of SEQ ID No.19 and the heavy chain CDR3 comprises the amino acid sequence of SEQ ID No.20; the heavy chain CDR1 comprises the amino acid sequence of SEQ ID No.26, the heavy chain CDR2 comprises the amino acid sequence of SEQ ID No.27 and the heavy chain CDR3 comprises the amino acid sequence of SEQ ID No.28; the heavy chain CDR1 comprises the amino acid sequence of SEQ ID No.34, the heavy chain CDR2 comprises the amino acid sequence of SEQ ID No.35 and the heavy chain CDR3 comprises the amino acid sequence of SEQ ID No.36; Or, the heavy chain CDR1 comprises the amino acid sequence of SEQ ID No.42, the heavy chain CDR2 comprises the amino acid sequence of SEQ ID No.43 and the heavy chain CDR3 comprises the amino acid sequence of SEQ ID No.44; the light chain CDR1 comprises the amino acid sequence of SEQ ID No.6, the light chain CDR2 comprises the amino acid sequence of SEQ ID No.7 and the light chain CDR3 comprises the amino acid sequence of SEQ ID No.8; the light chain CDR1 comprises the amino acid sequence of SEQ ID No.14, the light chain CDR2 comprises the amino acid sequence of SEQ ID No.15 and the light chain CDR3 comprises the amino acid sequence of SEQ ID No.16; the light chain CDR1 comprises the amino acid sequence of SEQ ID No.22, the light chain CDR2 comprises the amino acid sequence of SEQ ID No.23 and the light chain CDR3 comprises the amino acid sequence of SEQ ID No.24; the light chain CDR1 comprises the amino acid sequence of SEQ ID No.30, the light chain CDR2 comprises the amino acid sequence of SEQ ID No.31 and the light chain CDR3 comprises the amino acid sequence of SEQ ID No.32; the light chain CDR1 comprises the amino acid sequence of SEQ ID No.38, the light chain CDR2 comprises the amino acid sequence of SEQ ID No.39 and the light chain CDR3 comprises the amino acid sequence of SEQ ID No.40; Or, the light chain CDR1 comprises the amino acid sequence of SEQ ID No.46, the light chain CDR2 comprises the amino acid sequence of SEQ ID No.47 and the light chain CDR3 comprises the amino acid sequence of SEQ ID No.48.

Preferably, the heavy chain CDR1 comprises the amino acid sequence of SEQ ID No.2, the heavy chain CDR2 comprises the amino acid sequence of SEQ ID No.3 and the heavy chain CDR3 comprises the amino acid sequence of SEQ ID No.4; and, the light chain CDR1 comprises the amino acid sequence of SEQ ID No.6, the light chain CDR2 comprises the amino acid sequence of SEQ ID No.7 and the light chain CDR3 comprises the amino acid sequence of SEQ ID No.8; the heavy chain heavy chain CDR1 comprises the amino acid sequence of SEQ ID No.10, the heavy chain CDR2 comprises the amino acid sequence of SEQ ID No.11 and the heavy chain CDR3 comprises the amino acid sequence of SEQ ID No.12; and, the light chain CDR1 comprises the amino acid sequence of SEQ ID No.14, the light chain CDR2 comprises the amino acid sequence of SEQ ID No.15 and the light chain CDR3 comprises the amino acid sequence of SEQ ID No.16; the heavy chain CDR1 comprises the amino acid sequence of SEQ ID No.18, the heavy chain CDR2 comprises the amino acid sequence of SEQ ID No.19 and the heavy chain CDR3 comprises the amino acid sequence of SEQ ID No.20; and, the light chain CDR1 comprises the amino acid sequence of SEQ ID No.22, the light chain CDR2 comprises the amino acid sequence of SEQ ID No.23 and the light chain CDR3 comprises the amino acid sequence of SEQ ID No.24; the heavy chain CDR1 comprises the amino acid sequence of SEQ ID No.26, the heavy chain CDR2 comprises the amino acid sequence of SEQ ID No.27 and the heavy chain CDR3 comprises the amino acid sequence of SEQ ID No.28; and, the light chain CDR1 comprises the amino acid sequence of SEQ ID No.30, the light chain CDR2 comprises the amino acid sequence of SEQ ID No.31 and the light chain CDR3 comprises the amino acid sequence of SEQ ID No.32; the heavy chain CDR1 comprises the amino acid sequence of SEQ ID No.34, the heavy chain CDR2 comprises the amino acid sequence of SEQ ID No.35 and the heavy chain CDR3 comprises the amino acid sequence of SEQ ID No.36; and, the light chain CDR1 comprises the amino acid sequence of SEQ ID No.38, the light chain CDR2 comprises the amino acid sequence of SEQ ID No.39 and the light chain CDR3 comprises the amino acid sequence of SEQ ID No.40; Or, the heavy chain CDR1 comprises the amino acid sequence of SEQ ID No.42, the heavy chain CDR2 comprises the amino acid sequence of SEQ ID No.43 and the heavy chain CDR3 comprises the amino acid sequence of SEQ ID No.44; and, the light chain CDR1 comprises the amino acid sequence of SEQ ID No.46, the light chain CDR2 comprises the amino acid sequence of SEQ ID No.47 and the light chain CDR3 comprises the amino acid sequence of SEQ ID No.48.

The invention further provides an isolated protein comprising the heavy chain variable region of IL-13 antibody and/or light chain variable region of IL-13 antibody, the heavy chain variable region comprises the amino acid sequences of SEQ ID No.1, SEQ ID No.9, SEQ ID No.17, SEQ ID No.25, SEQ ID No.33 OR SEQ ID No.41; the light chain variable region comprises the amino acid sequences of SEQ ID No.5, SEQ ID No.13, SEQ ID No.21, SEQ ID No.29, SEQ ID No.37 or SEQ ID No.45.

Preferably, the heavy chain variable region comprises the amino acid sequence of SEQ ID No.1 and the light chain variable region comprises the amino acid sequence of SEQ ID No.5; the heavy chain variable region comprises the amino acid sequence of SEQ ID No.9 and the light chain variable region comprises the amino acid sequence of SEQ ID No.13; the heavy chain variable region comprises the amino acid sequence of SEQ ID No.17 and the light chain variable region comprises the amino acid sequence of SEQ ID No.21; the heavy chain variable region comprises the amino acid sequence of SEQ ID No.25 and the light chain variable region comprises the amino acid sequence of SEQ ID No.29; the heavy chain variable region comprises the amino acid sequence of SEQ ID No.33 and the light chain variable region comprises the amino acid sequence of SEQ ID No.37; Or, the heavy chain variable region comprises the amino acid sequence of SEQ ID No.41 and the light chain variable region comprises the amino acid sequence of SEQ ID No.45.

In summary, the numbers of the above-mentioned amino acid sequences are shown in Table 1:

TABLE 1

| | Amino acid sequence number of IL-13 antibody | | | | | | | |
|---|---|---|---|---|---|---|---|---|
| | Heavy chain protein | | | | Light chain protein | | | |
| Clone NO. | Variable region | CDR 1 | CDR 2 | CDR 3 | Variable region | CDR 1 | CDR 2 | CDR 3 |
| P4_4H12 | 1 | 2 | 3 | 4 | 5 | 6 | 7 | 8 |
| 29D9H8 | 9 | 10 | 11 | 12 | 13 | 14 | 15 | 16 |
| 28A2E11 | 17 | 18 | 19 | 20 | 21 | 22 | 23 | 24 |
| 35E2C3 | 25 | 26 | 27 | 28 | 29 | 30 | 31 | 32 |
| 70F10A10 | 33 | 34 | 35 | 36 | 37 | 38 | 39 | 40 |
| 35H6E1 | 41 | 42 | 43 | 44 | 45 | 46 | 47 | 48 |

Where the numbers in Table 1 are the sequence numbers of "SEQ ID No.", for example, the amino acid sequence of heavy chain variable region of P4_4H12 is shown in SEQ ID No. 1 of the sequence listing, and the amino acid sequence of the CDR1 domain in the heavy chain variable region of P4_4H12 is shown in SEQ ID No. 2 of the sequence listing.

Preferably, the protein further comprises a heavy chain constant region of antibody and/or a light chain constant region of antibody. The heavy chain constant region of antibody is conventional in the art, preferably a heavy chain constant region of human or mouse antibody, more preferably a heavy chain constant region of human antibody. The light chain constant region of antibody is conventional in the art, preferably a light chain constant region of human or mouse antibody, more preferably a light chain constant region of human antibody.

The protein is conventional protein in the art, preferably an IL-13 antibody, more preferably one or more of full-length antibody protein, antibody-antigen binding domain protein fragment, bispecific antibody, multispecific antibody, single-chain antibody fragment (scFv), single-domain (single-domain antibody, sdAb) or single-region antibody (Single-domain antibody), as well as the monoclonal antibody or polyclonal antibody prepared from aforesaid antibodies. The monoclonal antibody can be developed by a variety of routes and technologies such as hybridoma technology, phage display technology, single lymphocyte gene cloning technology and the like, and the production of monoclonal antibody from wild-type or transgenic mice by hybridoma technology is the current mainstream technology.

The full-length antibody protein is a conventional full-length antibody protein known in the art, which comprises a heavy chain variable region, a light chain variable region, a heavy chain constant region and a light chain constant region. Preferably, the heavy chain variable region and the light chain variable region of the protein, a human heavy chain constant region and a human light chain constant region form a human full-length antibody protein. Or preferably, the heavy chain variable region and the light chain variable region of the protein, a mouse heavy chain constant region and a mouse light chain constant region form a full-length antibody protein. Preferably, the full-length antibody protein is IgG1, IgG2, IgG3 or IgG4.

The single-chain antibody is a conventional single-chain antibody known in the art, which comprises a heavy chain variable region, a light chain variable region and a short peptide of 15-20 amino acids.

The protein fragment of antibody-antigen binding domain is a conventional protein fragment of antibody-antigen binding domain known in the art, which comprises a light chain variable region, a light chain constant region and a Fd fragment of a heavy chain constant region. Preferably, the protein fragment of antibody-antigen binding domain is Fab and F(ab')2.

The single-domain antibody is a conventional single-domain antibody known in the art, which comprises a heavy chain variable region and a heavy chain constant region.

The single-region antibody is a conventional single-region antibody known in the art, which only comprises a heavy chain variable region.

The preparation method of the protein is a conventional preparation method known in the art. The preparation method of the protein is preferably: isolating the protein from an expression transformant that recombinantly expresses the protein or artificially synthesizing the protein sequence of the protein. Preferably, the method for isolating the protein from the expression transformant that recombinantly expresses the protein includes: cloning a nucleic acid encoding the protein which comprises a point mutation into a recombinant vector, transforming the recombinant vector into the transformant to obtain a recombinant expression transformant, and isolating and purifying the protein from the culture of the recombinant expression transformant.

The present invention further provides a nucleic acid encoding aforesaid protein.

Preferably, the nucleic acids encoding the heavy chain variable region are shown in SEQ ID No.49, SEQ ID No.51, SEQ ID No.53, SEQ ID No.55, SEQ ID No.57 or SEQ ID No.59; and/or, the nucleic acids encoding the light chain variable region are shown in SEQ ID No.50, SEQ ID No.52, SEQ ID No.54, SEQ ID No.56, SEQ ID No.58 or SEQ ID No.60.

More preferably, the nucleic acid encoding the heavy chain variable region is shown in SEQ ID No.49, and the nucleic acid encoding the light chain variable region is shown in SEQ ID No.50; the nucleic acid encoding the heavy chain variable region is shown in SEQ ID No.51, and the nucleic acid encoding the light chain variable region is shown in SEQ ID No.52; the nucleic acid encoding the heavy chain variable region is shown in SEQ ID No.53, and the nucleic acid encoding the light chain variable region is shown in SEQ ID No.54; the nucleic acid encoding the heavy chain variable region is shown in SEQ ID No.55, and the nucleic acid encoding the light chain variable region is shown in SEQ ID No.56; the nucleic acid encoding the heavy chain variable region is shown in SEQ ID No.57, and the nucleic acid encoding the light chain variable region is shown in SEQ ID No.58; Or, the nucleic acid encoding the heavy chain variable region is shown in SEQ ID No.59, and the nucleic acid encoding the light chain variable region is shown in SEQ ID No.60.

In summary, the sequence ID numbers of the aforementioned nucleotide sequences are shown in Table 2:

TABLE 2

| Nucleotide SEQ ID No. of IL-13 Antibody | | |
|---|---|---|
| Clone No. | Heavy chain variable region of the protein | Light chain variable region of the protein |
| P4_4H12 | 49 | 50 |
| 29D9H8 | 51 | 52 |
| 28A2E11 | 53 | 54 |
| 35E2C3 | 55 | 56 |
| 70F10A10 | 57 | 58 |
| 35H6E1 | 59 | 60 |

Where the numbers in Table 2 are the sequence numbers of "SEQ ID No.", for example, the nucleotide sequence of heavy chain variable region of P4_4H12 is shown in SEQ ID No. 49 of the sequence listing, and the nucleotide sequence of heavy chain variable region of P4_4H12 is shown in SEQ ID No. 50 of the sequence listing.

The nucleotide sequence encoding the heavy chain CDR1 of P4_4H12 is the sequence from 91st to 105th base shown in SEQ ID No.49 of the Sequence Listing.

The nucleotide sequence encoding the heavy chain CDR2 of P4_4H12 is the sequence from 148th to 198th base shown in SEQ ID No.49 of the Sequence Listing.

The nucleotide sequence encoding the heavy chain CDR3 of P4_4H12 is the sequence from 295th to 348th base shown in SEQ ID No.49 of the Sequence Listing.

The nucleotide sequence encoding the light chain CDR1 of P4_4H12 is the sequence from 70th to 105th base shown in SEQ ID No.50 of the Sequence Listing.

The nucleotide sequence encoding the light chain CDR2 of P4_4H12 is the sequence from 151st to 171st base shown in SEQ ID No.50 of the Sequence Listing.

The nucleotide sequence encoding the light chain CDR3 of P4_4H12 is the sequence from 268th to 294th base shown in SEQ ID No.50 of the Sequence Listing.

The nucleotide sequence encoding the heavy chain CDR1 of 29D9H8 is the sequence from 91st to 105th base shown in SEQ ID No.51 of the Sequence Listing.

The nucleotide sequence encoding the heavy chain CDR2 of 29D9H8 is the sequence from 148th to 198th base shown in SEQ ID No.51 of the Sequence Listing.

The nucleotide sequence encoding the heavy chain CDR3 of 29D9H8 is the sequence from 295th to 327th base shown in SEQ ID No.51 of the Sequence Listing.

The nucleotide sequence encoding the light chain CDR1 of 29D9H8 is the sequence from 70th to 102nd base shown in SEQ ID No.52 of the Sequence Listing.

The nucleotide sequence encoding the light chain CDR2 of 29D9H8 is the sequence from 148th to 168th base shown in SEQ ID No.52 of the Sequence Listing.

The nucleotide sequence encoding the light chain CDR3 of 29D9H8 is the sequence from 265th to 291st base shown in SEQ ID No.52 of the Sequence Listing.

The nucleotide sequence encoding the heavy chain CDR1 of 28A2E11 is the sequence from 91st to 105th base shown in SEQ ID No.53 of the Sequence Listing.

The nucleotide sequence encoding the heavy chain CDR2 of 28A2E11 is the sequence from 148th to 198th base shown in SEQ ID No.53 of the Sequence Listing.

The nucleotide sequence encoding the heavy chain CDR3 of 28A2E11 is the sequence from 295th to 321st base shown in SEQ ID No.53 of the Sequence Listing.

The nucleotide sequence encoding the light chain CDR1 of 28A2E11 is the sequence from 67th to 108th base shown in SEQ ID No.54 of the Sequence Listing.

The nucleotide sequence encoding the light chain CDR2 of 28A2E11 is the sequence from 154th to 174th base shown in SEQ ID No.54 of the Sequence Listing.

The nucleotide sequence encoding the light chain CDR3 of 28A2E11 is the sequence from 271st to 297th base shown in SEQ ID No.54 of the Sequence Listing.

The nucleotide sequence encoding the heavy chain CDR1 of 35E2C3 is the sequence from 91st to 105th base shown in SEQ ID No.55 of the Sequence Listing.

The nucleotide sequence encoding the heavy chain CDR2 of 35E2C3 is the sequence from 148th to 195th base shown in SEQ ID No.55 of the Sequence Listing.

The nucleotide sequence encoding the heavy chain CDR3 of 35E2C3 is the sequence from 292nd to 321st base shown in SEQ ID No.55 of the Sequence Listing.

The nucleotide sequence encoding the light chain CDR1 of 35E2C3 is the sequence from 70th to 102nd base shown in SEQ ID No.56 of the Sequence Listing.

The nucleotide sequence encoding the light chain CDR2 of 35E2C3 is the sequence from 148th to 168th base shown in SEQ ID No.56 of the Sequence Listing.

The nucleotide sequence encoding the light chain CDR3 of 35E2C3 is the sequence from 265th to 291st base shown in SEQ ID No.56 of the Sequence Listing.

The nucleotide sequence encoding the heavy chain CDR1 of 70F10A10 is the sequence from 91st to 105th base shown in SEQ ID No.57 of the Sequence Listing.

The nucleotide sequence encoding the heavy chain CDR2 of 70F10A10 is the sequence from 148th to 198th base shown in SEQ ID No.57 of the Sequence Listing.

The nucleotide sequence encoding the heavy chain CDR3 of 70F10A10 is the sequence from 295th to 330th base shown in SEQ ID No.57 of the Sequence Listing.

The nucleotide sequence encoding the light chain CDR1 of 70F10A10 is the sequence from 70th to 120th base shown in SEQ ID No.58 of the Sequence Listing.

The nucleotide sequence encoding the light chain CDR2 of 70F10A10 is the sequence from 166th to 186th base shown in SEQ ID No.58 of the Sequence Listing.

The nucleotide sequence encoding the light chain CDR3 of 70F10A10 is the sequence from 283rd to 309th base shown in SEQ ID No.58 of the Sequence Listing.

The nucleotide sequence encoding the heavy chain CDR1 of 35H6E1 is the sequence from 91st to 111st base shown in SEQ ID No.59 of the Sequence Listing.

The nucleotide sequence encoding the heavy chain CDR2 of 35H6E1 is the sequence from 154th to 201st base shown in SEQ ID No.59 of the Sequence Listing.

The nucleotide sequence encoding the heavy chain CDR3 of 35H6E1 is the sequence from 298th to 336th base shown in SEQ ID No.59 of the Sequence Listing.

The nucleotide sequence encoding the light chain CDR1 of 35H6E1 is the sequence from 70th to 102th base shown in SEQ ID No.60 of the Sequence Listing.

The nucleotide sequence encoding the light chain CDR2 of 35H6E1 is the sequence from 148th to 168th base shown in SEQ ID No.60 of the Sequence Listing.

The nucleotide sequence encoding the light chain CDR3 of 35H6E1 is the sequence from 265th to 291st base shown in SEQ ID No.60 of the Sequence Listing. The preparation method of the nucleic acid is a conventional preparation method known in the art, preferably comprising following steps: the nucleic acid molecules encoding aforesaid proteins are obtained by gene cloning technology, or the nucleic acid molecules encoding aforesaid proteins are obtained by the method of artificial full sequence synthesis.

Person skilled in the art knows that the substitution, deletion, alteration, insertion or addition can be introduced into the base sequence encoding the amino acid sequence of aforesaid protein as appropriate to provide a homologue of polynucleotide. A homologue of polynucleotide in the present invention can be prepared by substituting, deleting or adding one or more bases of a gene encoding the protein sequence while the activity of the antibody is maintained.

The present invention further provides a recombinant expression vector comprising the nucleic acid.

As used herein, the recombinant expression vector can be obtained by the conventional method known in the art, that is, constructing the nucleic acid molecule of the present invention to various expression vectors. The expression vectors are a variety of vectors that are conventional in the art, as long as the vectors can accommodate aforesaid nucleic acid molecule. The vectors preferably include various plasmids, cosmids, phages or viral vectors.

The present invention further provides a recombinant expression transformant comprising the recombinant expression vector.

As used herein, the method for preparing the recombinant expression transformant is a conventional preparation method known in the art, preferably transforming the recombinant expression vector into host cells. The host cells are conventional various host cells known in the art, as long as they are able to stably self-replicate aforesaid recombinant expression vectors and efficiently express the carried nucleic acid. Preferably, the host cells are *E. coli* TG1 or *E. coli* BL21 cells (expressing single chain antibody or Fab antibody), or CHO-K1 cells (expressing full-length IgG antibody). The preferred recombinant expression transformant of the present invention can be obtained by transforming aforesaid recombinant expression plasmids into host cells. As used herein, the transformation method is a conventional method known in the art, preferably a chemical transformation method, a heat shock method or an electrotransformation method.

The present invention provides a method for preparing an IL-13 antibody, which comprises following steps: culturing the recombinant expression transformant, and obtaining the IL-13 antibody from the culture.

The present invention further provides a method for detecting cells that overexpressing an IL-13 protein, which comprises following steps: make a protein of claims 1-8 contact with a test sample in vitro, and detect the binding of the protein of claims 1-8 to the test sample.

The definition of overexpression is conventional overexpression in the art, which refers to the overexpression of RNA or protein of the IL-13 in the sample to be tested (due to increased transcription, post-transcriptional processing, translation, post-translational processing and the alternation in protein degradation), and local over-expression and improved functional activity (e.g. in the case of increased enzymatic hydrolysis of the substrate) resulting from changes in protein transporting patterns (increased nuclear localization).

As used herein, the method for a detection of aforesaid binding is the conventional method known in the art, preferably a detection by using fluorescence activated cell sorter (FACS).

The present invention provides a composition for detecting cells that overexpress the IL-13 protein, which comprises aforesaid protein as an active ingredient. Preferably, it further comprises a compound consisting of the functional fragments of aforesaid protein as an active ingredient.

The present invention provides a use of aforesaid protein in the preparation of a medicament.

Preferably, the medicament is a medicament for preventing or treating bronchial asthma.

The present invention further provides a pharmaceutical composition, the active ingredient of which comprises aforesaid protein.

The administration route of the pharmaceutical composition in the present invention is preferably administered by injection administration or oral administration. The injection administration preferably includes intravenous injection, intramuscular injection, intraperitoneal injection, intradermal injection or subcutaneous injection. The pharmaceutical composition is in various dosage forms conventionally known in the art, preferably in solid, semisolid or liquid form, and can be in aqueous solutions, non-aqueous solutions or suspensions, more preferably in tablets, capsules, granules, injections or infusions and the like.

Preferably, the pharmaceutical composition of the present invention further comprises one or more pharmaceutical carriers. The pharmaceutical carrier is the conventional pharmaceutical carrier known in the art, and the pharmaceutical carrier can be any suitable physiologically or pharmaceutically acceptable pharmaceutical adjuvant. The pharmaceutical adjuvant is a conventional pharmaceutical adjuvant known in the art, preferably includes pharmaceutically acceptable excipients, fillers, diluents and the like. More preferably, the pharmaceutical composition comprises 0.01-99.99% of aforesaid protein and 0.01-99.99% of the pharmaceutical carrier, and the percentage is the mass percentage of the pharmaceutical composition.

Preferably, the administration amount of the pharmaceutical composition is an effective amount that can alleviate or delay the progression of a disease, degenerative or traumatic disorder. The effective amount can be determined on an individual basis and will be based in part on a consideration of the symptoms to be treated and a outcome sought. The effective amount can be determined by person skilled in the art using aforesaid factors such as individual difference of subjects and conventional experimentation.

The present invention provides a use of aforesaid protein in preparing a medicament for preventing or treating disease associated with abnormal expression or dysfunction of IL-13.

In present invention, the disease associated with abnormal expression or dysfunction of IL-13 is conventional disease in the art. Preferably is bronchial asthma Based on the common knowledge in the art, aforesaid preferred conditions can be combined arbitrarily to obtain the preferable embodiments of the present invention.

The reagents and raw materials used in the present invention are commercially available.

The advantage of the present invention is that the protein of present invention, that is, provided IL-13 antibody, has high affinity, and the affinity of protein with human IL-13 protein reaches $KD<1\times10^{-8}M$. The protein of present invention can significantly inhibit the secretion induced by IL-13 in the thymus and activation-regulated chemokine (TARC) secretion assay and periostin secretion assay. It can significantly inhibit IL-13-induced expression through expressing vascular cells adhesion molecule-1 (VCAM-1) in human umbilical vein endothelial cells induced by IL-13. The protein of present invention blocks the binding of IL-13 to its ligand IL-13Ra1/IL-4Ra heterodimer and the binding of IL-13 to its ligand IL-13Ra2 heterodimer in the receptor-ligand binding-inhibition assays established by flow cytometry. In the animal model of airway inflammation induced by IL-13 in mice, it can significantly inhibit the airway respiratory inflammation and the airway hyperresponsiveness in mice induced by IL-13. It can be seen that the protein of the present invention, that is, the provided IL-13 antibody, can be applied to the preparation of a medicament for preventing or treating bronchial asthma.

BRIEF DESCRIPTION OF THE DRAWINGS

FIGS. 10A, 10B and 10C show the results of FACS for detecting the binding of IL-13 to the cell surface receptor IL-13Ra1/IL-4Ra heterodimer blocked by the leader antibody, chimeric antibody and human antibody, respectively.

DETAILED DESCRIPTION OF THE PREFERRED EMBODIMENT

Figure 1:
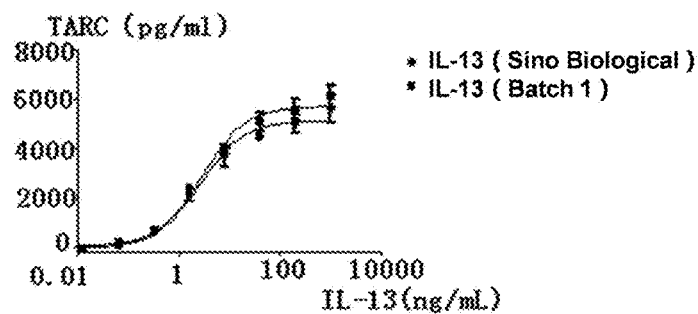
FIG. 1 shows the results of detecting the biological activity of IL-13 protein by the TARC secretion assay.

The present invention is further illustrated by the following embodiments, however, the present invention is not therefore limited to the scope of the described embodiments. The experimental methods that do not specify specific conditions in the following embodiments are selected according to conventional methods and conditions, or according to the manufacturer's instructions.

The term room temperature described in the following embodiments refers to the room temperature that is conventional in the art, and is generally 20-25° C.

Unless otherwise specified, the PBS buffer in the following embodiments is PBS phosphate buffer with pH 7.4.

Embodiment 1

Expression and Purification of Human IL-13 and Human IL-13R130Q Variants

A nucleotide encoding six histidines was added to the 3' end of the nucleotide sequence encoding Met1-Asn132 in the amino acid sequence of human IL-13 protein (see GenBank database, accession number: AAK53823.1) to obtain a nucleotide sequence of the recombinant human IL-13 protein with his tag (as shown in SEQ ID No. 61 of the Sequence Listing).

Alternatively, a nucleotide encoding six histidines was added to the 3' end of the nucleotide sequence encoding Met1-Asn132 in the amino acid sequence of human IL-13 protein variant IL-13 R130Q to obtain the nucleotide sequence of the recombinant human IL-13 R130Q variant with his tag (as shown in SEQ ID No. 62 of the Sequence Listing).

The nucleotide sequence encoding the recombinant human IL-13 protein with his tag and the nucleotide sequence of the recombinant human IL-13R130Q variant with his tag were cloned into a PCP vector (purchased from Invitrogen) respectively, and the plasmids were prepared according to established standard molecular biological methods as described in Sambrook, J., Fritsch, E. F., and Maniatis, T. (1989). Molecular Cloning: A Laboratory Manual, Second Edition (Plainview, N.Y.: Cold Spring Harbor Laboratory Press). FreeStyle 293F cells (purchased from Invitrogen) were transiently transfected (PEI, Polysciences) and expanded at 37° C. using FreeStyle™ 293 (purchased from Invitrogen). After 5-7 days, the cell culture was collected and centrifugated to remove cell components to obtain a supernatant containing his-labeled human IL-13 protein or his-labeled human IL-13R130Q variant. The aforementioned supernatants were loaded on a Ni-NTA affinity chromatography column (purchased from GE) respectively to purify the his-labeled human IL-13 (i.e., immunogen A) and the his-labeled human IL-13R1300 variant in the supernatants. Molecular sieve column (purchased from GE) was used for further purification to remove impurities such as macromolecular polymers. Purified immunogen A and his-labeled human IL-13R130Q variant were diluted in PBS phosphate buffer (pH 7.4), filtered through a 0.22 μm sterile filter, and sub-packed and stored at −80° C.

The purified immunogen A was subjected to a TARC secretion assay. Detailed method for TARC secretion assay was described in Miller et al. 2008, J Immunol Methods 334(1-2): 134-41.

A549 cells (purchased from ATCC) were cultured in F-12k medium (purchased from Gibco) containing 10% (w/w) fetal bovine serum, and expanded to 75-90% confluency in T-175 cell culture flask. The medium was aspirated completely, the cells were rinsed 1-2 times with PBS buffer and then digested with trypsin-EDTA (purchased from Life Technology) and collected. The collected cells were resuspended in the medium, and the cells were diluted to $2\times10^6$ cells/mL after counting and aliquoted to a 96-well cell culture plate ($2\times10^5$ cells per well) in an amount of 100 μL per well. The plates were incubated overnight in a 5% (v/v) $CO_2$ incubator at 37° C. On the second day, the gradient dilutions of immunogen A was mixed with recombinant human TNFα (purchased from Peprotech) to obtain a mixture I (wherein TNFα account for a final concentration of 200 ng/mL in the mixture I). After cultured overnight, the supernatant was discarded from the cell culture plate, and the above mixture I was pipetted in the cell culture plate for overnight cultured in a 5% (v/v) $CO_2$ incubator at 37° C. After 20 hours, the supernatant in the plate was aspirated, the cells were removed by centrifugation, and the concentration of TARC in the culture supernatant was determined using a TARC ELISA kit (purchased from RnD systems). The experimental procedure was carried out in accordance with the instructions of the kit.

The detailed experiment is briefly described as follows: The mouse anti-human TARC antibody was diluted to 2 μg/mL with PBS, and aliquoted into a 96-well microtiter plate in an amount of 100 μL per well incubation at 4° C. overnight. On the next day the plate was rinsed twice with the plate washing solution [PBS buffer containing 0.05% (w/w) Tween20], and the sample dilution [PBS buffer containing 1% (w/w) BSA] Liquid] was aliquoted into the plate at 300 μL per well. The plate was blocked at room temperature for 1 hour and the blocking solution was then removed. The standard was diluted to 500 μg/mL with the sample diluent and then double diluting six gradient concentration, and the sample diluent was used as blank control. Meanwhile, the culture supernatant was diluted 8 times with sample diluent. The standards and the samples were aliquoted to the plate at 100 μL per well and incubated at room temperature for 2 hours. The plate was rinsed 2-3 times with the washing solution. The biotin-labeled goat anti-human TARC antibody was diluted to a final concentration of 0.5 ng/mL with the sample diluent, and aliquoted into the microtiter plate at 100 μL per well. The plate was incubated at room temperature for 2 hours. The streptavidin labeled with the horseradish peroxidase (HRP) was diluted to a volume ratio of 1:200 with the sample diluent, and aliquoted into the plate at 100 μL per well. The plate was incubated at room temperature for 30 minutes and rinsed for 2-3 times with the washing solution. After the TMB substrate was aliquoted into plate at 100 μL per well and incubated at room temperature for 15 minutes, 50 μL of stop solution (1.0 N HCl) was aliquoted into each well. The $OD_{450\ nm}$ value was read by an ELISA plate reader (SpectraMax M5e, available from Molecular Device), then the absorbance value was calculated using the OD540 nm value as a background, and the TARC concentration in the culture supernatant was calculated. Some experimental results are shown in FIG. 1 and Table 3. Table 3 shows that immunogen A can stimulate the secretion of thymus and activation-regulated chemokine (TARC) by A549 cells, and the biological activity of immunogen A is basically consistent with that of commercial proteins.

TABLE 3

The biological activity of IL-13 protein was determined by TARC secretion assay

| TARC | IL-13 (ng/mL) | | | | | | | |
|---|---|---|---|---|---|---|---|---|
| (pg/mL) | 1000 | 200 | 40 | 8 | 1.6 | 0.32 | 0.06 | 0.01 |
| IL-13 (Sino Biological) | 5607.7 | 4968.5 | 4426.9 | 3662.6 | 2115.0 | 597.3 | 12.9 | −143.8 |
| IL-13 (Batch 1) | 6094.8 | 5577.7 | 5052.6 | 3952.4 | 2349.0 | 640.5 | 139.9 | −110.9 |

As used herein, the IL-13 (Sino Biological) means the commercial IL-13 protein, which is purchased from Sino biological and used as positive control; IL-13 (Batch 1) is the abovementioned immunogen A.

Embodiment 2

Obtain Lead Antibody by Phage Technology

1. Biotin Labeling of Immunogen A

Biotin-X-X-NHS (purchased from Sigma Aldrich) and the purified immunogen A prepared in embodiment 1 (hBLyS-ECD) were mixed at a molar ratio of 3:1 and stood for 30 minutes at room temperature. Subsequently, 50 mM final concentration of 1 M $NH_4Cl$ was pipetted to terminate the reaction and a biotin-labeled immunogen A was obtained. Later, the biotin-labeled immunogen A was then dialyzed in PBS phosphate buffer (pH 7.4). At last, broadford reagent (purchased from Pierce) was used and the concentration was determined using BSA as a standard sample (for details, see Bradford, 1976, Anal Biochem 72: 248-54). The experimental results are shown in Table 4. The $OD_{595\ nm}$ value of the biotin-labeled immunogen A is determined as 0.49, and the concentration of biotin-labeled immunogen A is calculated to be 0.319 mg/mL according to the curve fitted by the standard sample.

TABLE 4

Determination of the concentration of the biotin-labeled immunogen A

| $OD_{595nm}$ | Standard sample of protein (mg/ml) | | | | |
|---|---|---|---|---|---|
| | 0.5 | 0.25 | 0.125 | 0.05 | PBS buffer |
| Standard curve | 0.59 | 0.30 | 0.38 | 0.31 | 0.30 |
| Biotin-labeled immunogen A | 0.49 | | | — | |

The biotin-labeled immunogen A was filtered through a 0.22 μm of sterile filter, aseptically sub-packed, and stored at −80° C.

2. IL-13 Antibody Screening and Selection Using Phage Library (1) The immuno tubes were treated with streptavidin. Streptavidin (purchased from SIGMA-ALDRICH) was diluted to 12.5 μg/mL with PBS buffer, and aliquoted to the immuno tubes at 1 mL per tube. The immuno tubes were incubated at 4° C. overnight, and rinsed 3 times with PBS buffer to obtain treated immuno tubes.

(2) The biotin-labeled immunogen A obtained in step 1 was aliquoted into the treated immuno tubes, and the immuno tubes were shaken at room temperature for 1 hour, rinsed with PBS buffer, and then blocked with blocking solution [blocking solution is PBS buffer containing 2% (w/v) skim milk powder] at room temperature for 2 hours to obtain sample tubes. Meanwhile, a phage ScFv antibody library (the titer is about $10^{13}$ pfu/ml, purchased from Shanghai Chempartner Co., Ltd; or prepared reference to McCafferty J et al., Phage antibodies: flamentous phage displaying antibody variable domains, Nature, 1990, 348: 552-54; Smith G P, Filamentous fusion phage: novel expressing vectors that display cloned antigens on the virion surface, Science, 1985, 228:1315-1317; Scott J K et al., Searching for peptide ligands with an epitope library, Science, 1990, 249:386: the gene of a normal human antibody variable region was cloned into a phagemid vector, and then packaged into a phage by *E. coli* with the help of helper phage) was added to the treated immuno tubes, then the immuno tubes were shaken at room temperature for 1 hour, rinsed with PBS buffer, and then blocked with blocking solution at room temperature for 2 hours to obtain a blocked phage ScFv antibody library. Also set a control tube that only added the blocking solution at an equal volume of blocking solution in the sample tube. The blocking solution in the sample tube and the control tube were discarded, and the blocked phage ScFv antibody library was aliquoted to the tubes and shaken at room temperature for 2 hours. The tubes were rinsed 5 times with PBST [PBS buffer containing 0.1% (v/v) Tween20], and rinsed 5 times with PBS buffer to remove phage that did not bind to biotin-labeled immunogen A. Finally, 1 mL of 10 m/mL trypsin was aliquoted to each control tube and each sample tube, and the tubes were incubated for 30 minutes at 37° C. to elute the phage bound to biotin-labeled immunogen A to obtained the trypsin eluate.

(3) 1 mL of trypsin eluate was added to 4 mL of *E. coli* TG1 (purchased from LUCIGEN) in logarithmic growth phase and incubated at 37° C. for 30 minutes. Then the mixture was gradiently diluted and plated for an overnight incubation at 37° C. The number of clones bound to biotin-labeled immunogen A and the number of clones of the control tube were counted, and 20-30 clones were selected for sequencing respectively to obtain phage clones bound to immunogen A.

(4) The above-mentioned phage clones bound with immunogen A were washed with fresh 2YT medium (where the fresh 2YT medium was prepared by adding 10 g of yeast extract, 16 g of tryptone and 5 g of NaCl to 1 L of water, and adjusting the pH to 7.0 with NaOH and autoclaving), collected, and cultured at 37° C. with shaking until logarithmic phase. Helper phage M13K07 (purchased from NEB, Cat. No. N0315S) was added, mixed and stood at 37° C. for 30 minutes. Then, the solution was incubated with shaking at 37° C. for 30 minutes and centrifuged at 4000 rpm for 10 minutes. Subsequently, the cells precipitation were collected and added with fresh medium for resuspension, and incubated with shaking at 30° C. for 4 hours. After centrifugation at 4000 rpm for 30 minutes, the supernatant containing phage was collected, and ¼ volume of NaCl solution (2.5 M NaCl) containing 5×PEG was added and allowed for placing on ice overnight to obtain treated supernatant A. On the next day, after centrifuging the supernatant A at 4000 rpm for 10 minutes to remove residual impurities such as cells and debris, the treated phage A was collected for biopanning in the next round.

The above steps (3) to (4) were repeated for three to four rounds, and phage clones bound with immunogen A were selected from the plates picked in the third or fourth round, and cultured in fresh medium to logarithmic growth phase. Phage clones that bind with immunogen A in supernatant A after treatment were screened by ELISA and sequenced. Phage clones having a strong binding capacity ($OD_{450\ nm}$>1.0) and containing a unique single-chain antibody sequence were further screened using receptor-ligand inhibition assay. That is, the phage clones having a strong binding ability ($OD_{450\ nm}$>1.0) and reaching 60% inhibitory rate of blocking the binding of human IL-13 to hIL-13Ra/hIL-4R heterodimer and/or hIL-13Ra2 receptor in the receptor-ligand binding-inhibition assay were selected to be positive, and then the amino acid sequence of which was determined. A positive clone having an only amino acid sequence was selected, and a human antibody was prepared based on the previously determined nucleotide sequence and the corresponding amino acid sequence (see embodiments 5, 6 and 7 for detailed procedures). Wherein, the partial results of the receptor-ligand binding-inhibition assay are shown in Table 5. The ratio of 1:5 and the like means the dilution of the sample. For example, 1:5 means that the sample to be tested (i.e., the supernatant A containing the phage clone bound with immunogen A) was diluted to a volume 5 times the original volume. The results in Table 5 indicate that the lead antibody with clone No. P4_4H12 can block the binding of IL-13 to the cell surface receptor IL-13Ra1/IL-4Ra heterodimer, but cannot block the binding of IL-13 to the cell surface receptor IL-13Ra2, which had unique properties.

TABLE 5

FACS detection of phage clones blocking the binding of IL-13 to cell surface receptor IL-13Ra1/IL-4Ra heterodimer and blocking the binding of IL-13 to cell surface receptor IL-13Ra2

| Clone No. | hIL-13Ra1/hIL-4Ra-overexpressing 293 cells | | | hIL-13Ra2 overexpressing 293 cells | | |
|---|---|---|---|---|---|---|
| | 1:1 | 1:5 | 1:25 | 1:1 | 1:10 | 1:100 |
| P4_4H12 | 88.7% | 71.7% | 30.8% | −11.7% | −6.9% | −5.6% |

Embodiment 3

Obtain Lead Antibody Using Hybridoma Technology

1. Mouse Immunization

Figure 2:
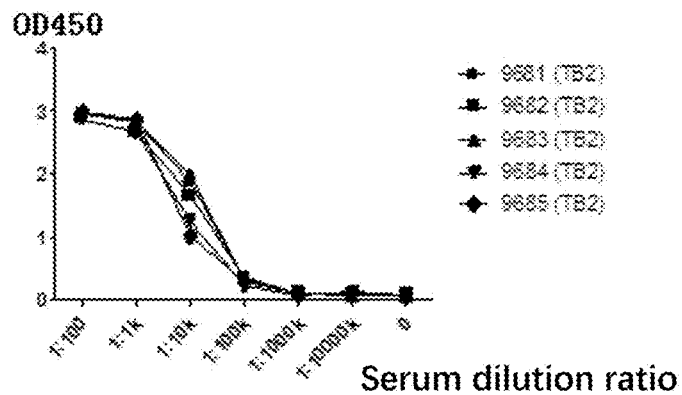
FIG. 2 shows the results of ELISA for detecting the antibody titers of mouse serum after immunized with immunogen A.

Immunogen A was used to immunize Balb/c, SJL/J mice (supplied by Shanghai SLAC Laboratory Animal Co., Ltd.) aged 6-8 weeks. Mice were feed under Specific pathogen Free (SPF) conditions after received. The initial immunization dose was 50 μg of immunogen A per mouse. The protein was emulsified in Freund's complete adjuvant and 0.25 mL of which was injected subcutaneously into the tail. 2 weeks after the initial immunization, the immunization was boosted. Immunogen A (25 μg per mouse) was emulsified in Freund's incomplete adjuvant and 0.25 mL of which was intraperitoneally injected. The interval of each booster immunization was three weeks. Serum samples were collected one week after each booster immunization, and the antibody titer in the serum was tested by ELISA and the activity of the antibody in the serum was measured by receptor-ligand binding-inhibition assay. Mice with higher serum titers and better blocking the binding of immunogen A to the receptor would be preferred for cell fusion and hybridoma cell preparation, and the rest of mice continued to be immunization boosted for later use. Some experimental results are shown in FIG. 2 and Table 6. Table 6 shows that the serum of mice immunized with immunogen A have different degrees of binding to immunogen A, exhibiting an antigen-antibody reaction. Among them, the highest dilution (i.e., dilution fold) of serum is about 100,000. The blank control in Table 6 refers to 1% (w/w) BSA, and the batch TB2 refers to the serum of the mice on the seventh day after the second booster immunization. The data in the table are the $OD_{450\ nm}$ value.

TABLE 6

ELISA detection of serum antibody titer of mice immunized with immunization A

| $OD_{450\ nm}$ Batch | Serum dilution ratio | | | | | | Blank control |
|---|---|---|---|---|---|---|---|
| | 1:100 | 1:10³ | 1:10⁴ | 1:10⁵ | 1:10⁶ | 1:10⁷ | |
| 9681 (TB2) | 2.96 | 2.83 | 1.87 | 0.33 | 0.1 | 0.08 | 0.06 |
| 9682 (TB2) | 2.87 | 2.65 | 1.65 | 0.35 | 0.1 | 0.07 | 0.07 |
| 9683 (TB2) | 2.99 | 2.83 | 1.98 | 0.33 | 0.09 | 0.06 | 0.06 |
| 9684 (TB2) | 2.87 | 2.66 | 1.25 | 0.22 | 0.08 | 0.12 | 0.08 |
| 9685 (TB2) | 2.98 | 2.85 | 1.01 | 0.29 | 0.09 | 0.09 | 0.06 |

Gene immunization was used. The PCP expression vector expressing the recombinant human IL-13 protein constructed in embodiment 1 was coated on a 1.0 μm gold colloidal bullet and immunized with a Helios gene gun (Bio-rad). Gold colloidal bullet preparation and immunization procedures were formulated according to the Helios gene gun instructions. Female SJL/J mice (supplied by Shanghai SLAC Laboratory Animal Co., Ltd.) aged 6-8 weeks were feed under SPF conditions after received. All mice were immunized 3-4 times with a gene gun through the abdomen, 3-4 shots each time with 1.0 μg of plasmid per shot. The interval between the initial immunization and the first booster was 2 weeks, and the interval between each booster was 3 weeks. Serum samples were collected 7 days after each booster, antibody titers in serum were detected by ELISA and the activity of the antibody in serum was tested by receptor-ligand binding-inhibition assay. Mice with higher serum titers and better blocking the binding of recombinant human IL-13 protein to the receptor will be preferred for cell fusion and hybridoma cell preparation, and the rest of mice continued to be boosted for the later use.

2. Preparation of Hybridoma Cells and Screening of Lead Antibody

Most mice that were immunized with immunogen A can achieve a titer of 1:1000 or more after 2-3 immunizations, which was sufficient to collect lymphocytes for cell fusion and hybridoma preparation.

Prior to cell fusion, each mouse was immunized with 50-100 μg of immunogen A for the last immunization. 3-5 days later the mice were sacrificed and spleen cells were collected. NH₄OH was aliquoted to a final concentration of 1% (w/w) to lysis the red blood cells in the spleen cell suspension, and the cells were centrifugally washing with DMEM basal medium for 2-3 times and mixed with the mouse myeloma cells SP2/0 (purchased from ATCC) at a ratio of 5:1. Cell fusion was carried out using a conventional PEG cell fusion method or a high-efficiency electrofusion method (see METHODS IN ENZYMOLOGY, VOL. 220) to obtain fused cells, i.e., hybridoma cells.

The fused cells were diluted into DMEM selective medium containing 20% (w/w) fetal bovine serum and 1×HAT, and aliquoted into a 96-well cell culture plate at 1×10⁵/20 μL per well. Then the plate was placed in 5% (v/v) CO₂ incubator at 37° C. After 10-14 days, the supernatant in the cell fusion was screened by ELISA, and the positive clones with $OD_{450\ nm}$>1.0 in ELISA were expanded cultured in a 24-well plate. After 2-3 days, the supernatant in the 24-well plate was retested, e.g. the binding activity of antibody in supernatant to immunogen A was determined by ELISA, the binding activity of human IL-13 to its receptor blocking by the antibody in the supernatant was analyzed by flow cytometry, and the biological activity of the antibody in the supernatant neutralizing by immunogen A was determined by A549 thymus and activation-regulated chemokine (TARC) secretion assay. Hybridoma cells with $OD_{450\ nm}$>1.0 in ELISA assay, inhibition rate reaching 60% in receptor-ligand binding-inhibition assay (the inhibition rate herein indicates the percentage of the combination between human IL-13 and hIL-13Ra/hIL-4R heterodimers and/or hIL-13Ra2 receptor inhibited by supernatant of hybridoma cell culture), and/or the inhibition rate in A549 thymus activation regulatory chemokine (TARC) secretion assay reaching 60% (the inhibition rate here is the inhibition rate of hybridoma supernatant neutralizing TARC secretion induced by human IL-13) were selected as positive clones.

According to the screening results of the 24-well plate samples, qualified positive clones were selected and subcloned in a 96-well plate by limited dilution method, i.e., the above positive clones were cultured in DMEM medium (purchased from invitrogen) containing 10% (w/w) FBS at 37° C. under conditions of 5% (v/v) $CO_2$. Primary screening was performed by ELISA 7-10 days after subcloning, and 3-4 positive monoclonal clones were selected and expanded into 24-well plates for further culture. After 2-3 days, the supernatant was retested according to the test method of subclones, including ELISA, receptor-ligand binding-inhibition assay, and thymus and activation-regulated chemokine secretion assay. According to the detection results of samples from 24-well plate, the optimal subclones were selected for expanded culture, liquid nitrogen cryopreservation, antibody production and purification to obtain lead antibodies. The clone numbers of these lead antibodies are 29D9H8, 28A2E11, 35E2C3, 70F10A10 and 35H6E1, respectively.

Embodiment 4

Production and Purification of Monoclonal Antibodies from Mouse Hybridoma Cells

The hybridoma cells prepared in Embodiment 3 were expanded into T-75 cell culture flasks and domesticated for 2-3 passages using a production medium (Hybridoma serum free medium, purchased from Invitrogen). The hybridoma cells grew in good condition were inoculated into culture spinner flasks. 200-500 mL of production medium was added into each of 2 liters of culture spinner flasks, and the cells were inoculated at a density of $0.5$-$1.0\times10^5$ cells/mL. Close the cap tightly and place the spinner flasks on a roller shaker in a 37° C. incubator and adjust to a speed of 3 rpm/min. After 10-14 days of continuous spinning culture, the cell culture medium was collected, centrifuged or filtered to remove the cells, and filtered through a 0.22-0.45 μm filter. The treated cell culture supernatant can be immediately purified or frozen at −30° C.

The monoclonal antibody in the hybridoma cells culture supernatant can be purified by Protein G affinity chromatography (Protein G, Protein G column) column. According to the size of the sample volume, a corresponding volume of the column was prepared. For 200-300 mL of small volume purification, 1-2 mL of Protein G column was required. The Protein G column was first equilibrated with an equilibration buffer (PBS buffer, pH 7.4) and the culture supernatant was loaded on the Protein G column with a flow rate of 3-4 mL/min. After loading, the column was washed with 3-5 times of the bed volume of equilibration buffer. The antibody bound to the column was eluted with elution buffer (0.1M glycine hydrochloride buffer, pH 2.5), and the elution was monitored with an ultraviolet detector. Eluted antibody (according to the A280 UV absorption peak) was collected, the pH was neutralized by adding 10% (v/v) 1.0 M Tris-HCl buffer, and then the elution was immediately dialyzed overnight with PBS buffer. The next day the buffer was changed once and dialysis was continued for 2-3 hours. The dialyzed antibody was collected and sterile-filtered using a 0.22 μm filter to obtain an IL-13 monoclonal antibody, which was aseptically stored. Samples were sub-packed for later detection and analysis of protein concentration, purity and endotoxin. It was found that the endotoxin concentration of the IL-13 monoclonal antibody was less than 3.0 EU/mg. Partial results of the detection and analysis are shown in Table 7.

TABLE 7

Antibody detection and analysis

| Clone No. | Antibody concentration | Protein concentration (mg/mL) | Endotoxin (EU/mg) |
|---|---|---|---|
| 29D9H8 | >90% | 0.56 | 2.9 |
| 28A2E11 | >90% | 0.59 | <0.2 |
| 35E2C3 | >90% | 0.26 | 0.67 |
| 70F10A10 | >90% | 0.49 | 0.75 |
| 35H6E1 | >90% | 0.81 | 0.81 |

Example 5 Determination of Lead Antibody

The lead antibodies obtained in Embodiment 2 and Embodiment 3 using the phage technique and the hybridoma technique were used for the following assays, respectively.

A. Enzyme-Linked Immunosorbent Assay (ELISA) was Used to Detect the Binding of Lead Antibody to Immunogen A, IL-13R130Q Variant, Cynomolgus IL-13 and Mouse IL-13.

Figure 3A:
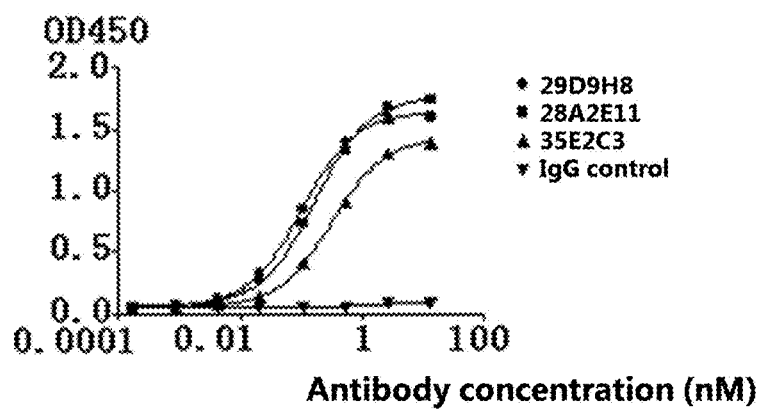
FIGS. 3A, 3B and 3C show the results of ELISA for detecting the reactivity of the lead antibody, the chimeric antibody and human antibody with immunogen A respectively.
Figure 3B:
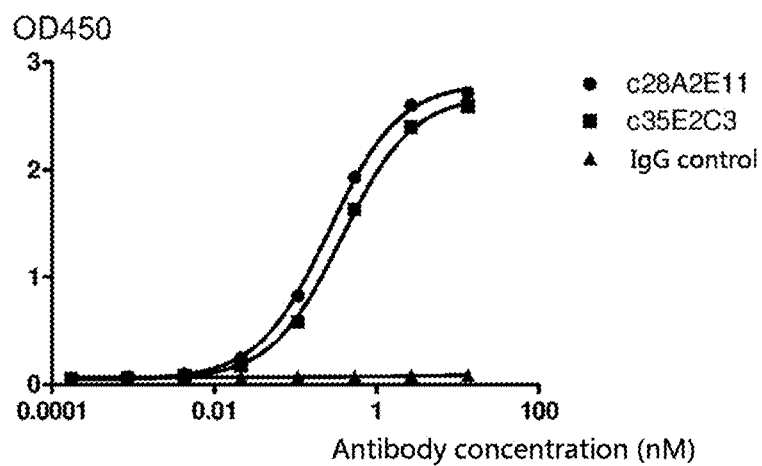
Figure 3C:
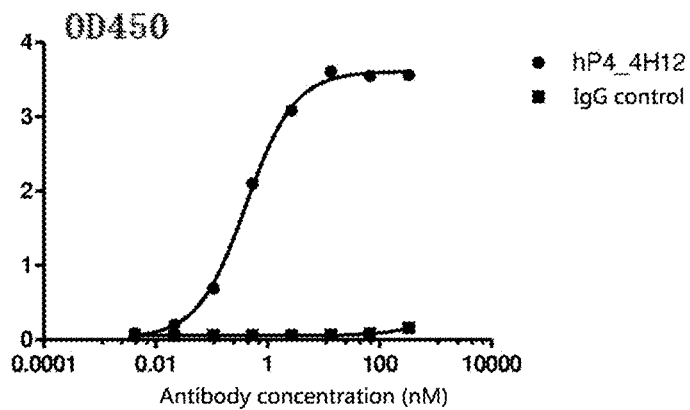
Figure 5A:
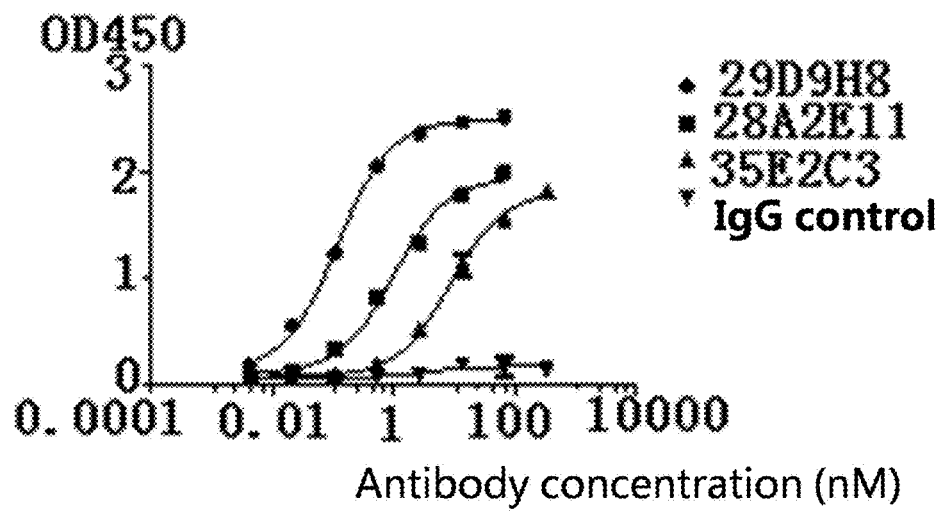
FIGS. 5A and 5B is the results of ELISA for detecting the reactivity of the lead antibody and the chimeric antibody with cynomolgus IL-13 respectively.
Figure 5B:
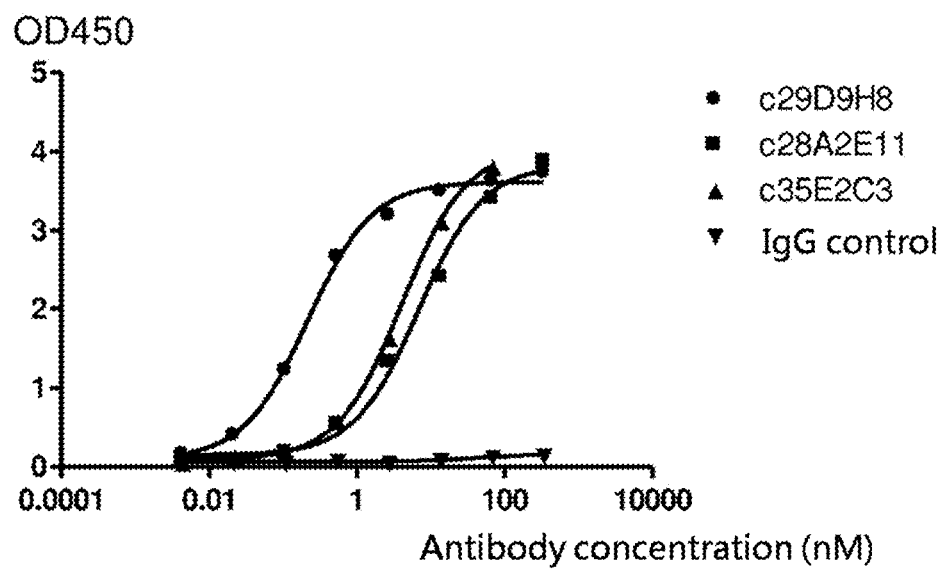
Figure 6:
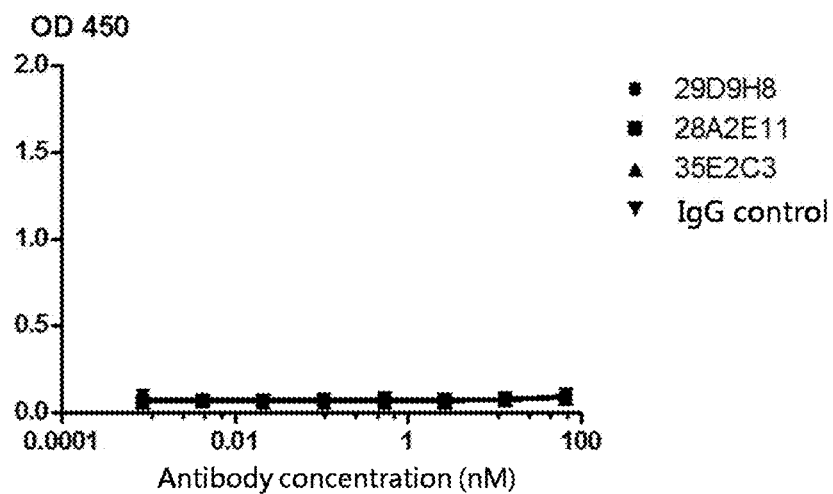
FIG. 6 shows the results of ELISA for detecting the reactivity of the lead antibody with murine IL-13.

Streptavidin was diluted with PBS to a final concentration of 1.0 μg/mL, and then aliquoted into a 96-well microtiter plate at 100 μl per well. The plate was incubated at 4° C. overnight, on the next day, the plate was rinsed twice with washing solution [PBS containing 0.05% (w/w) Tween 20], and blocking solution [containing 0.05% (w/w) Tween 20 and 2% (w/w) BSA in PBS buffer] was aliquoted into the plate for blocking at 37° C. for 1-2 hours. The blocking solution was discarded, and the biotin-labeled immunogen A prepared in Embodiment 2, IL-13R130Q variant (prepared in Embodiment 1), cynomolgus IL-13 (purchased from sino biological) and mouse IL-13 (purchased from sino biological) were diluted to 0.5 μg/mL with sample solution [PBS buffer containing 0.05% (w/w) Tween 20 and 0.2% (w/w) BSA] respectively, and aliquoted into the plate at 50-100 μL per well. The plate was incubated at 37° C. for 1 hour and rinsed 2-3 times with washing solution [PBS buffer containing 0.01% (w/w) Tween20]. The gradient-diluted lead antibodies prepared in Embodiment 2 and Embodiment 3 were aliquoted into the plate at 50-100 μL per well, and after incubating at 37° C. for 1 hour, the plate was rinsed 2-3 times with washing solution. Horseradish peroxidase (HRP)-labeled human or mouse IgG secondary antibody (purchased from Sigma) was aliquoted, and after incubating at 37° C. for 1 hour, the plate was rinsed 2-3 times with washing solution [PBS buffer containing 0.05% (w/w) Tween20]. 100 μL/well of TMB substrate was aliquoted and the plate was incubated at room temperature for 15 minutes, followed by aliquoting 50 μL of 1.0 N HCl to each well to terminate the reaction. The $ID_{450\ nm}$ value was read using an ELISA plate reader (SpectraMax M5e, available from Molecular Device). Some experimental results are shown in FIGS. 3, 5-6 and Tables 8-11. Tables 8-11 illustrate that the lead antibodies bind to recombinant human IL-13 protein, recombinant human IL-13 R130Q variant, and recombinant cynomolgus IL-13 at the ELISA level. However, they do not bind to mouse IL-13. As used herein, the IgG control is mouse IgG, and the data in the table are the $OD_{450\ nm}$ value.

TABLE 8

ELISA detection of the reactivity of lead antibody with immunogen A

| $OD_{450\ nm}$ | Antibody concentration (nM) | | | | | | | |
|---|---|---|---|---|---|---|---|---|
| Clone No. | 13.33 | 2.67 | 0.53 | 0.11 | 0.021 | 0.004 | 0.001 | 0.000 |
| 29D9H8 | 1.60 | 1.61 | 1.40 | 0.85 | 0.34 | 0.12 | 0.07 | 0.06 |
| 28A2E11 | 1.74 | 1.69 | 1.32 | 0.74 | 0.28 | 0.10 | 0.07 | 0.05 |
| 35E2C3 | 1.39 | 1.31 | 0.91 | 0.41 | 0.15 | 0.07 | 0.05 | 0.05 |
| IgG Control | 0.09 | 0.08 | 0.06 | 0.05 | 0.05 | 0.05 | 0.05 | 0.05 |

TABLE 9

ELISA detection of the reactivity of lead antibody with cynomolgus IL-13 variant

| $OD_{450nm}$ | Antibody concentration (nM) | | | | | | |
|---|---|---|---|---|---|---|---|
| Clone No. | 66.67 | 13.33 | 2.67 | 0.53 | 0.11 | 0.021 | 0.004 |
| 29D9H8 | 2.52 | 2.46 | 2.36 | 2.05 | 1.24 | 0.56 | 0.19 |
| 28A2E11 | 1.99 | 1.78 | 1.35 | 0.83 | 0.35 | 0.14 | 0.08 |
| 35E2C3 | 1.56 | 1.13 | 0.52 | 0.21 | 0.11 | 0.07 | 0.07 |
| IgG 对照 | 0.18 | 0.21 | 0.10 | 0.09 | 0.07 | 0.07 | 0.07 |

TABLE 10

ELISA detection of the reactivity of lead antibody with mouse IL-13 variant

| $OD_{450nm}$ | Antibody concentration (nM) | | | | | | | |
|---|---|---|---|---|---|---|---|---|
| Clone No. | 13.33 | 2.67 | 0.53 | 0.11 | 0.021 | 0.004 | 0.001 | 0.000 |
| 29D9H8 | 0.09 | 0.07 | 0.06 | 0.07 | 0.06 | 0.07 | 0.07 | 0.07 |
| 28A2E11 | 0.08 | 0.08 | 0.07 | 0.07 | 0.08 | 0.07 | 0.06 | 0.07 |
| 35E2C3 | 0.09 | 0.08 | 0.06 | 0.06 | 0.06 | 0.06 | 0.07 | 0.07 |
| IgG 对照 | 0.10 | 0.08 | 0.08 | 0.08 | 0.07 | 0.07 | 0.07 | 0.10 |

B. Receptor-Ligand Binding-Inhibition Assay

Figure 7:
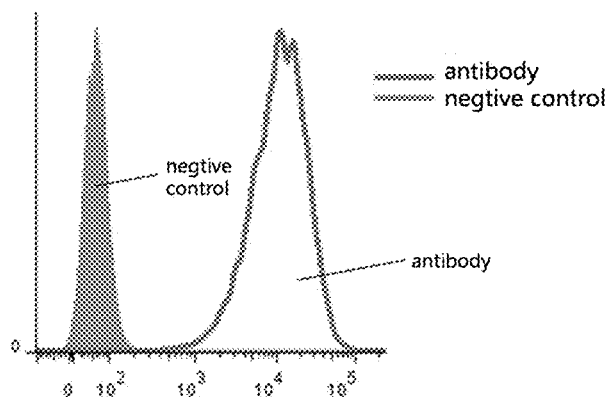
FIG. 7 is the results of flow cytometric for analyzing the expression level of hIL-13Ra1 protein in a HEK293 cell line overexpressing full-length human IL-13Ra1. As used herein, the antibody refers to a goat anti-human IL-13Ra1 antibody (purchased from RnD systems); the negative control refers to a goat IgG control.
Figure 8:
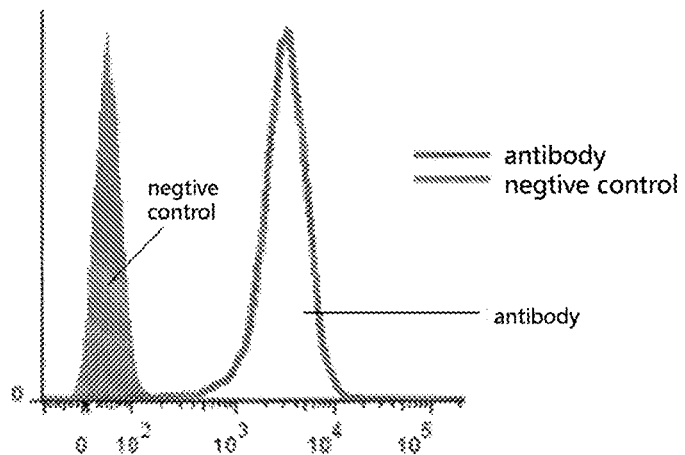
FIG. 8 is the results of flow cytometric for analyzing the expression level of hIL-4Ra protein in a HEK293 cell line overexpressing full-length human IL-4Ra. As used herein, the antibody refers to a mouse anti-human IL-4Ra antibody (purchased from RnD systems); the negative control refers to a mouse IgG control.
Figure 9:
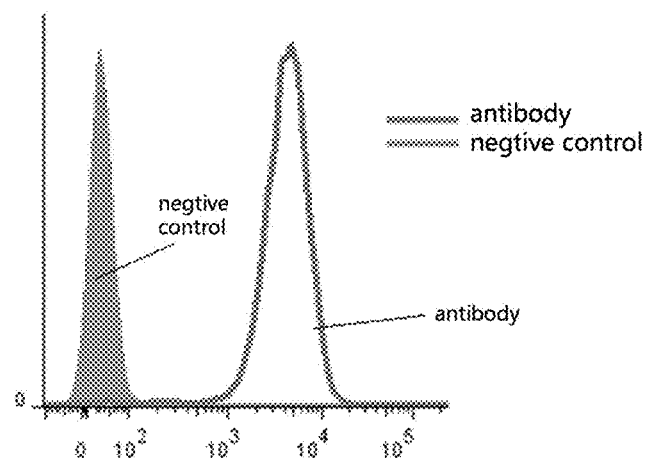
FIG. 9 is the results of flow cytometric for analyzing the expression level of hIL-13Ra2 protein in a HEK293 cell line overexpressing full-length human IL-13Ra2. As used herein, the antibody refers to a goat anti-human IL-13Ra2 antibody (purchased from RnD systems); the negative control refers to a goat IgG control.

1. Construction of Stable Expression Cell Lines:

The nucleotide sequences of human IL-13Ra1, human IL-13Ra2 and human IL-4Ra full-length genes (as shown in SEQ ID No. 63-65 of the sequence listing) were cloned into pIRES expression vector respectively and packaged into lentiviruses (the pIRES expression vector and lentivirus were purchased from Shanghai Genepharma Technology Co., Ltd. and operated according to the instructions). HEK293 cells were simultaneously infected with lentivirus containing the human IL-13Ra1 and human IL-4Ra genes, and the cells were cultured in DMEM medium containing one or two of 100 μg/mL Hygromycin B (purchased from MILLIPORE) and 0.25 μg/mL Puromycin (purchased from Invitrogen), and 10% (w/w) fetal bovine serum at 37° C. with 5% (v/v) $CO_2$ for 2 weeks. After 2 weeks, the infected cells were subcloned into 96-well culture plate by limited dilution. After the clones grew up, the monoclonal cells were expanded into 6-well plates or culture flasks to obtain a HEK293 cell line expressing full-length human IL-13Ra1 and a HEK293 cell line expressing full-length human IL-4Ra. For expanded clones, the expression levels of receptor and binding ability to the ligand IL-13 protein were detected by flow cytometry using specific antibodies (hIL-13Ra1 antibody, hIL-4Ra antibody and hIL-13Ra2 antibody were purchased from RnD systems) corresponding to each receptor. Monoclonal cell lines with better growth, higher expression levels, and stronger binding were selected for further expansion culture and cryopreserved in liquid nitrogen. HEK293 cells were infected with lentiviral particles containing human IL-13Ra2 gene, and HEK293 cell line overexpressing full length human IL-13Ra2, which was obtained by screening and selecting the monoclonal cell lines with good growth, high expression level and strong binding in the same manner, was expanded and stored in liquid nitrogen. Some experimental results are shown in FIGS. 7-9 and Tables 11-13. The results of Tables 11-13 indicate that the surface of HEK293 cell clone 4C1 simultaneously expresses hIL-13Ra1 and hIL-4Ra receptors, HEK293 cell clone 1A1 expresses hIL-13Ra2 receptor, and both expression levels of cell surface receptors are high, indicating that they can be used for subsequent assays.

TABLE 11

Flow cytometric analysis of hIL-13Ra1 protein expression level in HEK293 cell line overexpressing full-length human IL-13Ra1

| | hIL-13Ra1 antibody | | IgG subtype control | |
|---|---|---|---|---|
| Clone No. of transfected cell | Mean fluorescence intensity | Positive cell (%) | Mean fluorescence intensity | Positive cell (%) |
| 4C1 | 9952 | 100 | 55.8 | 0 |

TABLE 12

Flow cytometric analysis of hIL-4Ra protein expression level in HEK293 cell line overexpressing full-length human IL-4Ra

| | hIL-4Ra antibody | | IgG subtype control |
|---|---|---|---|
| Clone No. of transfected cell | Mean fluorescence intensity | Positive cell (%) | Mean fluorescence intensity |
| 4C1 | 2746 | 99 | 39.5 | 0 |

TABLE 13

Flow cytometric analysis of hIL-13Ra2 protein expression level in HEK293 cell line overexpressing full-length human IL-13Ra2

| | hIL-13Ra2 antibody | | IgG subtype control |
|---|---|---|---|
| Clone No. of transfected cell | Mean fluorescence intensity | Positive cell (%) | Mean fluorescence intensity |
| 1A1 | 3745 | 99 | 26.8 | 0 |

2. Receptor-Ligand Binding-Inhibition Assay Using Flow Cytometry

HEK293 cell line clone 4C1 overexpressing full-length human IL-13Ra1 and human IL-4Ra and HEK293 cell line clone 1A1 overexpressing full-length human IL-13Ra2 obtained from step 1 of experiment B in Embodiment 5 were expanded and cultured to 75-90% confluency in T-175 cell culture flask and the medium was aspirated. Among them, the medium for expanded culture is the DMEM medium containing one or two of 100 μg/mL Hygromycin B (purchased from MILLIPORE) and 0.25 μg/mL Puromycin (purchased from Invitrogen) and 10% (w/w) fetal bovine serum. The conditions for culture expanding were 37° C. and 5% (v/v) $CO_2$. Cells were rinsed 1-2 times with PBS buffer, then digested with recombinant enzyme cell dissociation buffer (TrypLE, purchased from Life technology) and collected. Cells was rinsed 1-2 times with PBS buffer, and diluted to 1-2×10$^6$ cells/mL with blocking solution [PBS buffer containing 2% (w/w) fetal bovine serum] after counting. Later, cells were incubated on ice for 20-30 minutes, and rinsed twice with blocking solution [PBS buffer containing 2% (w/w)) fetal bovine serum]. The collected cells were suspended to 1×10$^6$ cells/mL with a blocking solution, and aliquoted to a 96-well FACS reaction plate at 100 μL per well (i.e., 1×10$^5$ cells per well).

Figure 10A:
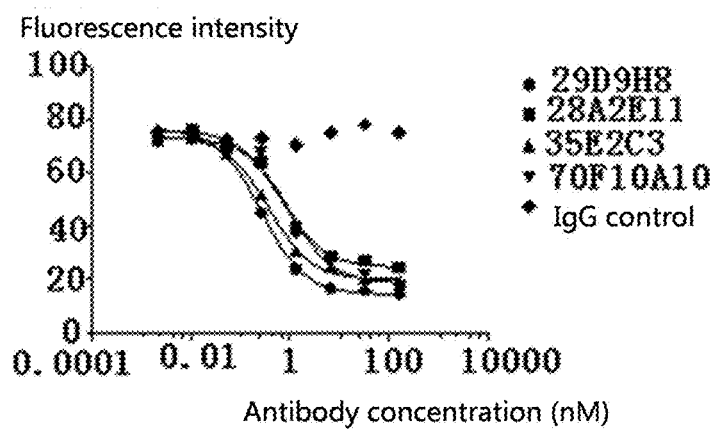
Figure 10B:
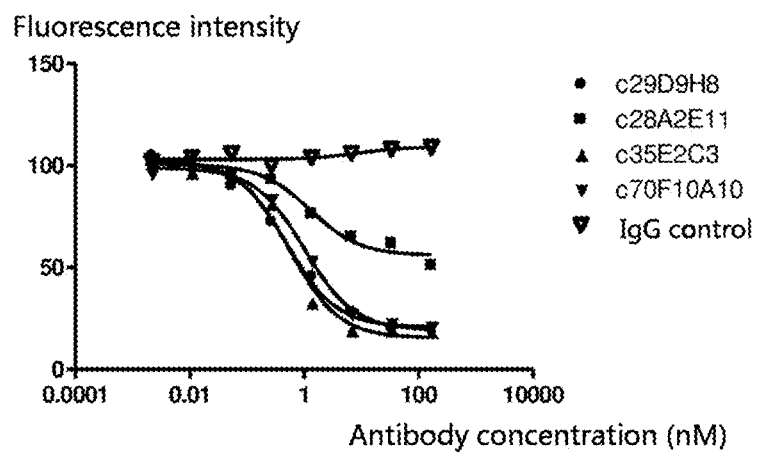
Figure 11A:
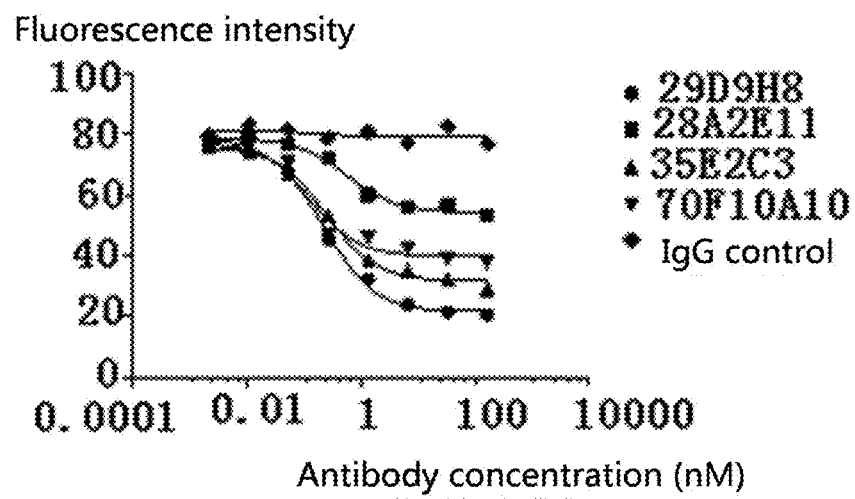
FIGS. 11A, 11B and 11C show the results of FACS for detecting the binding of IL-13 to the cell surface receptor IL-13Ra blocked by the leader antibody, chimeric antibody and human antibody, respectively.
Figure 11B:
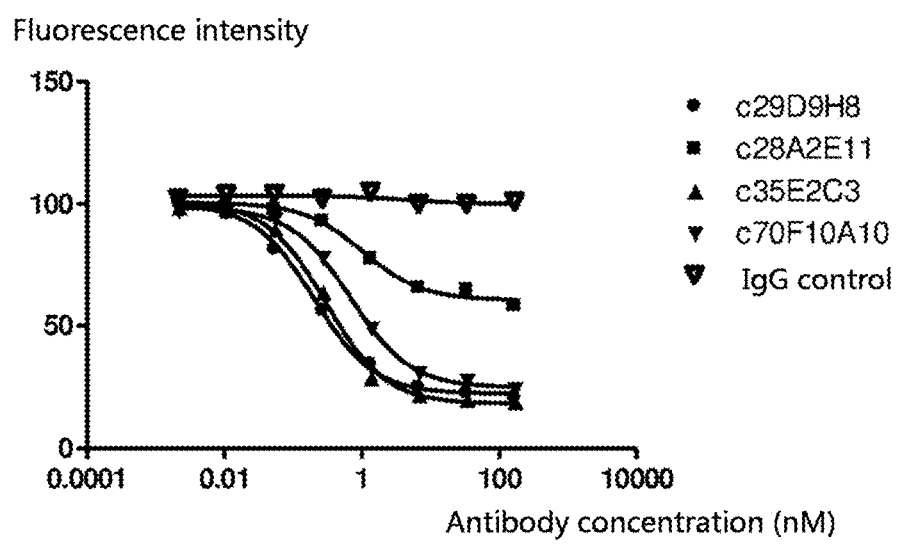
Figure 11C:
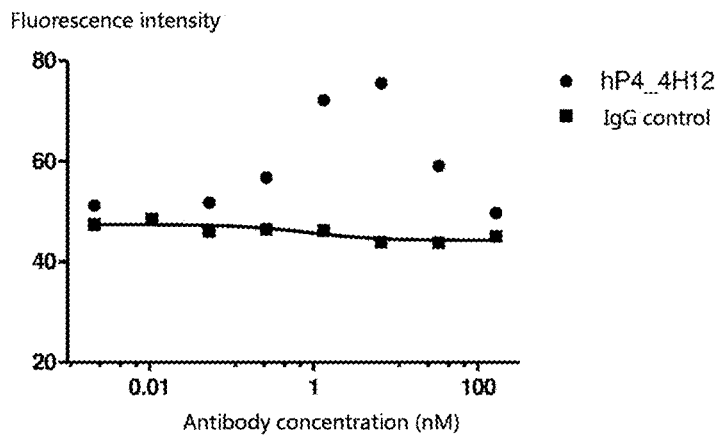

The gradient-diluted lead antibody prepared in Embodiment 2 and Embodiment 3 (hereinafter referred as "lead antibody") was mixed with the biotin-labeled immunogen A prepared in Embodiment 2, then aliquoted to the cells at 100 μL per well, and incubated on ice for 1-2 hours. Among them, the HEK293 cell line overexpressing the full-length human IL-13Ra1 and human IL-4Ra obtained in the step 1 of experiment B in Embodiment 5 was added with a gradient-diluted lead antibody and biotin-labeled immunogen A with a final concentration of 30 ng/mL. For HEK293 cell lines overexpressing full-length human IL-13Ra2, the gradient-diluted lead antibody and biotin-labeled immunogen A with a final concentration of 20 ng/mL were added. Later, the mixture was rinsed twice with a blocking solution, and added with the fluorescent (Alexa 488)-labeled streptavidin (purchased from Life Technology, Cat. No. 511223) at 100 μL per well and incubated on ice for 0.5-1.0 hours. Next, the cells were rinsed 2-3 times with blocking solution, PBS buffer was aliquoted to suspend the cells at 100 μL per well, and the results were detected and analyzed with FACS (FACS Verse, available from BD). Some experimental results are shown in FIGS. 10-11 and Tables 14-15. Tables 14-15 show that the binding of IL-13 antibody to human IL-13 can block the binding of human IL-13 to cell surface receptor IL-13Ra1/hIL-4Ra heterodimer, or the binding of IL-13 to the cell surface human IL-13Ra2 receptor. The IgG control is mouse IgG and the data in the table are the mean fluorescence intensity.

TABLE 14

FACS detection of lead antibody blocking the binding of IL-13 to cell surface receptor IL-13Ra1/IL-4Ra heterodimer

| fluorescence intensity | Antibody concentration (nM) | | | | | | | |
|---|---|---|---|---|---|---|---|---|
| Clone No. | 166.67 | 33.33 | 6.67 | 1.33 | 0.27 | 0.05 | 0.01 | 0.002 |
| 29D9H8 | 14.8 | 15.9 | 16.6 | 24 | 45.3 | 68.5 | 74.2 | 75.3 |
| 28A2E11 | 24.6 | 27.2 | 28.8 | 39.6 | 64.2 | 71.5 | 76.2 | 74.7 |
| 70F10A10 | 19.3 | 20.3 | 24.7 | 30.7 | 51.9 | 67.6 | 73.5 | 72.5 |
| IgG control | 17.1 | 22.1 | 27.7 | 37.5 | 67.9 | 68.9 | 72.4 | 72 |

TABLE 15

FACS detection of lead antibody blocking the binding of IL-13 to cell surface receptor IL-13Ra2

| fluorescence intensity | Antibody concentration (nM) | | | | | | | |
|---|---|---|---|---|---|---|---|---|
| Clone No. | 166.67 | 33.33 | 6.67 | 1.33 | 0.27 | 0.05 | 0.01 | 0.002 |
| 29D9H8 | 20.5 | 21.5 | 23.6 | 32.3 | 45.4 | 67.6 | 74.6 | 76.3 |
| 28A2E11 | 53.3 | 56.6 | 55.9 | 60.1 | 72.1 | 76.9 | 79.7 | 76.5 |
| 35E2C3 | 28.9 | 32.4 | 35.1 | 38.7 | 53.2 | 66.6 | 74.3 | 76 |
| 70F10A10 | 37.8 | 39.1 | 42.3 | 46 | 46.8 | 70.8 | 75.6 | 76.7 |
| IgG control | 77 | 82.7 | 77.2 | 80.7 | 78.9 | 81.3 | 83.2 | 79.3 |

C, Secretion Assay of Thymus and Activation Regulating Chemokine (TARC)

Figure 12A:
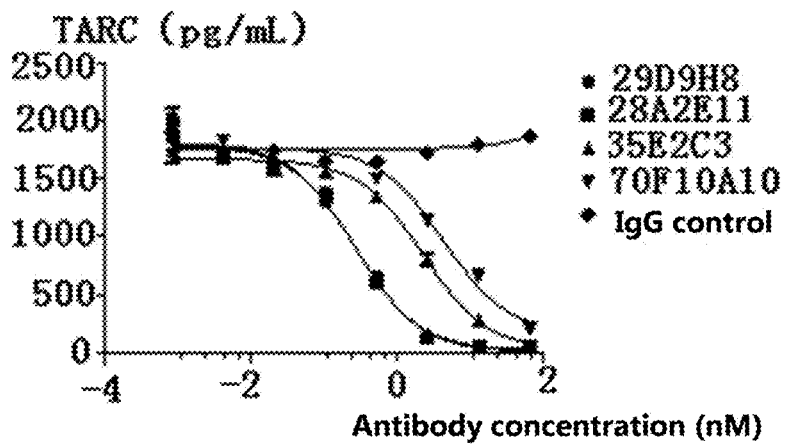
FIGS. 12A, 12B and 12C show the results of IL-13-induced secretion of thymus and activation-regulated chemokine neutralized by the leader antibody, chimeric antibody and human antibody, respectively.
Figure 12B:
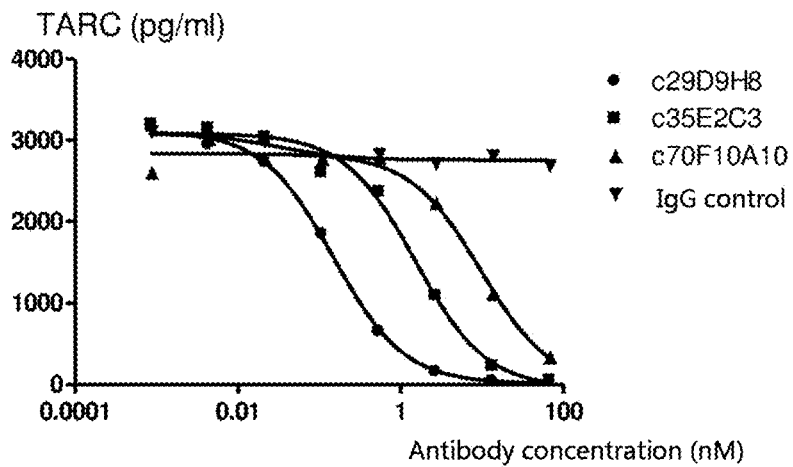
Figure 12C:
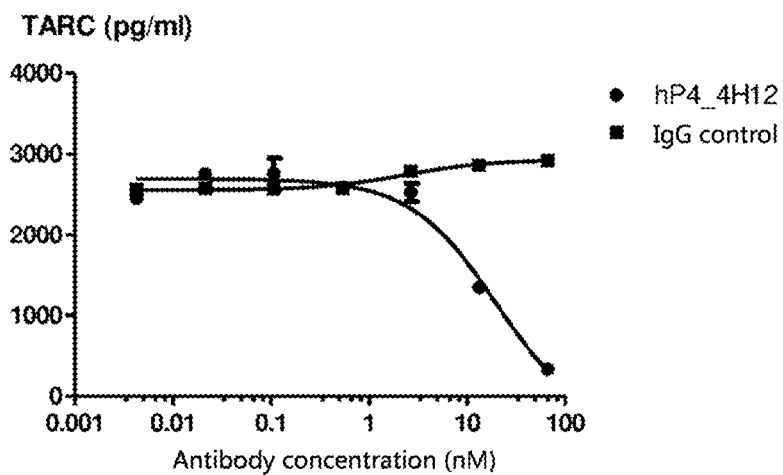

A549 cells (purchased from ATCC) were cultured in F-12k medium (purchased from Gibco) containing 10% (w/w) fetal bovine serum at 37° C., 5% (v/v) $CO_2$, and expanded into T-175 cell culture flask when the cells was cultured to 75-90% confluency. Then the medium was aspirated, and the cells was rinsed 1-2 times with PBS buffer. After that, the cells were digested with trypsin-EDTA (purchased from Life Technology) and collected. The collected cells were resuspended in the medium, and the cells were diluted to $2 \times 10^6$ cells/mL after counting, and aliquoted into a 96-well cell culture plate at 100 μL per well ($2 \times 10^5$ cells per well). Subsequently, the plate was incubated overnight at 37° C. in a 5% (v/v) CO 2 incubator. On the next day, the gradient-diluted lead antibody prepared in Embodiment 2 and Embodiment 3 were mixed with the immunogen A prepared in Embodiment 1 to obtain a mixture A. The recombinant human TNFα (purchased from Peprotech) was then mixed with F-12k medium containing 10% (w/w) fetal bovine serum in an equal volume to obtain a mixture B. After that, the final concentration of the mixed recombinant human TNFα in the mixture B was 200 ng/mL. After aspirating the supernatant of the cell culture plate incubated overnight, the above mixture A and mixture B were aliquoted into the cell culture plate in a 1:1 volume ratio. As used herein, the final concentration of the immunogen A in the total volume of the mixture A and the mixture B was 5 ng/mL, and the final concentration of the recombinant human TNFα in the total volume of the mixture A and the mixture B was 200 ng/mL. Later, the cell culture plate was incubated overnight at 37° C. in a 5% (v/v) $CO_2$ incubator. After 20 hours, the culture supernatant in the plate was aspirated, the cells were removed by centrifugation, and the concentration of TARC in the culture supernatant was determined using a TARC ELISA kit (purchased from RnD systems). The experimental protocol was carried out in accordance with the instructions of the kit (see Embodiment 1 for details). Some experimental results are shown in FIG. 12 and Table 16. Table 16 shows that the binding of the lead antibody to human IL-13 can neutralize the secretion of TARC by 549 cells induced by IL-13 and TNFα co-stimulation. The data in Table 16 show the concentration (pg/ml) of TARC in the culture supernatant, wherein the IgG control is mouse IgG.

then allowed to stand at room temperature for 5 minutes and added with 0.2 mL of chloroform. Later, the tube was shaken for 15 seconds, stood for 2 minutes and centrifuged at 12000 g for 5 minutes at 4° C., and the supernatant of the tube was transferred to a new 1.5 mL centrifuge tube. Next, 0.5 mL of isopropanol was added in, and the liquid in the tube was gently mixed. After standing at room temperature for 10 minutes, the tube was centrifuged at 12000 g for 15 minutes at 4° C., and the supernatant was discarded. Then 1 mL of 75% (v/v) ethanol was added, the precipitate was rinsed gently and centrifugated at 12000 g for 5 minutes at 4° C., and the supernatant was discarded. At last, the precipitate was dried and dissolved by adding in the DEPC-treated $H_2O$ (55° C. water bath to dissolve for 10 minutes), thereby the total RNA was obtained.

Reverse transcription and PCR: 1 μg of total RNA and the reverse transcriptase were added for the establishment of a 20 μL reaction system. After maitaining at 42° C. for 60 minutes, the reaction was terminated at 7° C. for 10 minutes. A 50 μL PCR system was setup comprising 1 μL of cDNA, 25 pmol of each primer, 1 μL of DNA polymerase, 250 μmol of dNTPs and a compatible buffer system. PCR program was set as pre-denaturing at 95° C. for 3 minutes, 35 cycles of denaturing at 95° C. for 30 seconds, annealing at 55° C. for 30 seconds and extending at 72° C. for 35 seconds, followed by extension at 72° C. for 5 minutes to obtain a PCR product. The kit used for reverse transcription was PrimeScript RT Master Mix (purchased from Takara, Cat. No. RR036), and the kit used for PCR including the Q5 high-fidelity enzyme was purchased from NEB (Cat. No. M0492).

Cloning and sequencing: 5 μL of PCR product was taken for agarose gel electrophoresis, and positive samples were purified by column recovery kit NucleoSpin® Gel & PCR Clean-up, purchased from MACHEREY-NAGEL with a Cat. No. of 740609. Ligation was carried out by using 50 ng of sample, 50 ng of T vector, 0.5 μL of recombinase Exnase, 1 μL of buffer being brought to a final reaction system volume of 10 μL, and reacted at 16° C. for half an hour to obtain the ligated product, wherein the ligation kit is T4 DNA ligase purchased from NEB with a Cat. No. of M0402. 5 μL of the ligation product was pipetted into 100 μL of competent cells (Ecos 101competent cells, purchased from Yeastern, Cat. No. FYE607) and ice-cooled for 5 minutes. Subsequently the competent cells were heat shocked at 42°

TABLE 16

Lead antibody neutralized IL-13-induced TARC secretion

| TARC (pg/mL) | Antibody concentration ( nM) | | | | | | |
|---|---|---|---|---|---|---|---|
| Clone NO. | 66.7 | 13.3 | 2.7 | 0.5 | 0.11 | 0.021 | 0.004 | 0.001 |
| 29D9H8 | 42 | 53 | 146 | 653 | 1298 | 1595 | 1720 | 1913 |
| 28A2E11 | 56 | 51 | 118 | 601 | 1359 | 1586 | 1695 | 1852 |
| 35E2C3 | 67 | 278 | 797 | 1339 | 1549 | 1615 | 1671 | 1732 |
| 70F10A10 | 207 | 656 | 1144 | 1500 | 1628 | 1603 | 1829 | 2002 |
| IgG control | 1866 | 1796 | 1721 | 1645 | 1648 | 1741 | 1724 | 2011 |

Embodiment 6

Determination of Amino Acid Sequences in the Light Chain Variable Region and Heavy Chain Variable Region Isolation of total RNA: The hybridoma cells corresponding to the lead antibody prepared in Embodiment 3 were thawed and cultured, then centrifugated to collect $1-5 \times 10^7$ cells. Subsequently, the cells were mixed with 1 mL of Trizol and transferred to a 1.5 mL centrifuge tube. The tube was C. for 1 minute in water bath and placed back on ice for 1 minutes, then 650 μL of antibiotic-free SOC medium was added and the competent cells were resuscitated at 200 RPM for 30 minutes on a shaker at 37° C., and 200 μL of cells suspension was pipetted and plating on LB solid medium containing antibiotic and incubated overnight in an incubator at 37° C. On the next day, colony PCR was performed in a 30 μL PCR system using primers M13F and M13R accommodated with T vector, bacterial colonies were picked by a tip and pipetted into the PCR system and mixed, and 0.5 µL of suspension was picked onto another LB solid plate containing 100 nM ampicillin to preserve the bacterial strain. 5 µL of product was taken for the detection of agarose gel electrophoresis when the PCR reaction is completed, and the positive samples were sequenced. As used herein, the protocol of sequencing references to Kabat, Sequences of Proteins of Immunological Interest, National Institutes of Health, Bethesda, Md. (1991).

The sequencing results are shown in Tables 17-18. Tables 17-18 also include the sequencing results of the IL-13 antibody with the clone No. P4_4H12 obtained in Embodiment 2.

TABLE 17

Amino acid sequence number of IL-13 antibody

| Clone NO. | Heavy chain protein | | | | Light chain protein | | | |
| --- | --- | --- | --- | --- | --- | --- | --- | --- |
| | Variable region | CDR 1 | CDR 2 | CDR 3 | Variable region | CDR 1 | CDR 2 | CDR 3 |
| P4_4H12 | 1 | 2 | 3 | 4 | 5 | 6 | 7 | 8 |
| 29D9H8 | 9 | 10 | 11 | 12 | 13 | 14 | 15 | 16 |
| 28A2E11 | 17 | 18 | 19 | 20 | 21 | 22 | 23 | 24 |
| 35E2C3 | 25 | 26 | 27 | 28 | 29 | 30 | 31 | 32 |
| 70F10A10 | 33 | 34 | 35 | 36 | 37 | 38 | 39 | 40 |
| 35H6E1 | 41 | 42 | 43 | 44 | 45 | 46 | 47 | 48 |

As used herein, the numbers in Table 17 are the sequence numbers of "SEQ ID No.", for example, the amino acid sequence of heavy chain variable region of P4_4H12 is shown in SEQ ID No. 1 of the sequence listing, and the amino acid sequence of CDR1 region in the heavy chain variable region of P4_4H12 is shown in SEQ ID No. 2 of the sequence listing.

TABLE 18

Nucleotide sequence number of IL-13 antibody

| Clone NO. | Variable region of heavy chain | Variable region of light chain |
| --- | --- | --- |
| P4_4H12 | 49 | 50 |
| 29D9H8 | 51 | 52 |
| 28A2E11 | 53 | 54 |
| 35E2C3 | 55 | 56 |
| 70F10A10 | 57 | 58 |
| 35H6E1 | 59 | 60 |

As used herein, the numbers in Table 18 are the sequence numbers of "SEQ ID No.", for example, the nucleotide sequence of heavy chain variable region of P4_4H12 is shown in SEQ ID No. 49 of the sequence listing, and the nucleotide sequence of heavy chain variable region of P4_4H12 is shown in SEQ ID No. 50 of the sequence listing.

The nucleotide sequence encoding the heavy chain CDR1 of P4_4H12 is the sequence from 91st to 105th base shown in SEQ ID No.49 of the Sequence Listing.

The nucleotide sequence encoding the heavy chain CDR2 of P4_4H12 is the sequence from 148th to 198th base shown in SEQ ID No.49 of the Sequence Listing.

The nucleotide sequence encoding the heavy chain CDR3 of P4_4H12 is the sequence from 295th to 348th base shown in SEQ ID No.49 of the Sequence Listing.

The nucleotide sequence encoding the light chain CDR1 of P4_4H12 is the sequence from 70th to 105th base shown in SEQ ID No.50 of the Sequence Listing.

The nucleotide sequence encoding the light chain CDR2 of P4_4H12 is the sequence from 151st to 171st base shown in SEQ ID No.50 of the Sequence Listing.

The nucleotide sequence encoding the light chain CDR3 of P4_4H12 is the sequence from 268th to 294th base shown in SEQ ID No.50 of the Sequence Listing.

The nucleotide sequence encoding the heavy chain CDR1 of 29D9H8 is the sequence from 91st to 105th base shown in SEQ ID No.51 of the Sequence Listing.

The nucleotide sequence encoding the heavy chain CDR2 of 29D9H8 is the sequence from 148th to 198th base shown in SEQ ID No.51 of the Sequence Listing.

The nucleotide sequence encoding the heavy chain CDR3 of 29D9H8 is the sequence from 295th to 327th base shown in SEQ ID No.51 of the Sequence Listing.

The nucleotide sequence encoding the light chain CDR1 of 29D9H8 is the sequence from 70th to 102nd base shown in SEQ ID No.52 of the Sequence Listing.

The nucleotide sequence encoding the light chain CDR2 of 29D9H8 is the sequence from 148th to 168th base shown in SEQ ID No.52 of the Sequence Listing.

The nucleotide sequence encoding the light chain CDR3 of 29D9H8 is the sequence from 265th to 291st base shown in SEQ ID No.52 of the Sequence Listing.

The nucleotide sequence encoding the heavy chain CDR1 of 28A2E11 is the sequence from 91st to 105th base shown in SEQ ID No.53 of the Sequence Listing.

The nucleotide sequence encoding the heavy chain CDR2 of 28A2E11 is the sequence from 148th to 198th base shown in SEQ ID No.53 of the Sequence Listing.

The nucleotide sequence encoding the heavy chain CDR3 of 28A2E11 is the sequence from 295th to 321st base shown in SEQ ID No.53 of the Sequence Listing.

The nucleotide sequence encoding the light chain CDR1 of 28A2E11 is the sequence from 67th to 108th base shown in SEQ ID No.54 of the Sequence Listing.

The nucleotide sequence encoding the light chain CDR2 of 28A2E11 is the sequence from 154th to 174th base shown in SEQ ID No.54 of the Sequence Listing.

The nucleotide sequence encoding the light chain CDR3 of 28A2E11 is the sequence from 271st to 297th base shown in SEQ ID No.54 of the Sequence Listing.

The nucleotide sequence encoding the heavy chain CDR1 of 35E2C3 is the sequence from 91st to 105th base shown in SEQ ID No.55 of the Sequence Listing.

The nucleotide sequence encoding the heavy chain CDR2 of 35E2C3 is the sequence from 148th to 195th base shown in SEQ ID No.55 of the Sequence Listing.

The nucleotide sequence encoding the heavy chain CDR3 of 35E2C3 is the sequence from 292nd to 321st base shown in SEQ ID No.55 of the Sequence Listing.

The nucleotide sequence encoding the light chain CDR1 of 35E2C3 is the sequence from 70th to 102nd base shown in SEQ ID No.56 of the Sequence Listing.

The nucleotide sequence encoding the light chain CDR2 of 35E2C3 is the sequence from 148th to 168th base shown in SEQ ID No.56 of the Sequence Listing.

The nucleotide sequence encoding the light chain CDR3 of 35E2C3 is the sequence from 265th to 291st base shown in SEQ ID No.56 of the Sequence Listing.

The nucleotide sequence encoding the heavy chain CDR1 of 70F10A10 is the sequence from 91st to 105th base shown in SEQ ID No.57 of the Sequence Listing.

The nucleotide sequence encoding the heavy chain CDR2 of 70F10A10 is the sequence from 148th to 198th base shown in SEQ ID No.57 of the Sequence Listing.

The nucleotide sequence encoding the heavy chain CDR3 of 70F10A10 is the sequence from 295th to 330th base shown in SEQ ID No.57 of the Sequence Listing.

The nucleotide sequence encoding the light chain CDR1 of 70F10A10 is the sequence from 70th to 120th base shown in SEQ ID No.58 of the Sequence Listing.

The nucleotide sequence encoding the light chain CDR2 of 70F10A10 is the sequence from 166th to 186th base shown in SEQ ID No.58 of the Sequence Listing.

The nucleotide sequence encoding the light chain CDR3 of 70F10A10 is the sequence from 283rd to 309th base shown in SEQ ID No.58 of the Sequence Listing.

The nucleotide sequence encoding the heavy chain CDR1 of 35H6E1 is the sequence from 91st to 111st base shown in SEQ ID No.59 of the Sequence Listing.

The nucleotide sequence encoding the heavy chain CDR2 of 35H6E1 is the sequence from 154th to 201st base shown in SEQ ID No.59 of the Sequence Listing.

The nucleotide sequence encoding the heavy chain CDR3 of 35H6E1 is the sequence from 298th to 336th base shown in SEQ ID No.59 of the Sequence Listing.

The nucleotide sequence encoding the light chain CDR1 of 35H6E1 is the sequence from 70th to 102th base shown in SEQ ID No.60 of the Sequence Listing.

The nucleotide sequence encoding the light chain CDR2 of 35H6E1 is the sequence from 148th to 168th base shown in SEQ ID No.60 of the Sequence Listing.

The nucleotide sequence encoding the light chain CDR3 of 35H6E1 is the sequence from 265th to 291st base shown in SEQ ID No.60 of the Sequence Listing.

Embodiment 7

Preparation of Mouse-Human Chimeric IL-13 Antibody or Fully Human IL-13 Antibody The positive clone had been obtained from the phage library in Embodiment 2, and the purified IL-13 antibody (lead antibody) had been obtained from the culture supernatant of the hybridoma cells in Embodiment 3. Here, according to the protocol described in the present embodiment, a mouse-human chimeric IL-13 antibody can be prepared from the lead antibody obtained in Embodiment 3; and a fully human IL-13 antibody can be prepared from the positive clone obtained in Embodiment 2.

1. Plasmids Construction and Preparation:

The sequences of heavy chain variable region and light chain variable region of IL-13 antibody were defined according to the sequencing results of Embodiment 6. The sequence of heavy chain variable region of the lead antibodies obtained in Embodiment 2 and Embodiment 3 were recombined into an expression vector comprising a signal peptide and a constant region of human heavy chain antibody IgG1 (wherein the expression vector was purchased from Invitrogen, and the recombination step was also performed by Shanghai Chempartner Co., Ltd) respectively, the sequence of light chain variable region of the IL-13 antibodies were recombined into an expression vector comprising a signal peptide and a light chain kappa constant region of human antibody (wherein the expression vector was purchased from Invitrogen, and the recombination step was also performed by Shanghai Chempartner Co., Ltd) respectively, and recombinant plasmids were obtained (the experimental principle and protocols of the above plasmid recombination were shown in Molecular Cloning: A Laboratory Manual, Third Edition, (American) J. SAMBROOK etc.) and confirmed by sequencing (the sequencing method was the same as that in Embodiment 6). The recombinant plasmids with a high purity were extracted by using a medium-scale alkaline lysis kit (purchased from MACHEREY-NA-GEL), with a mass of 500 μg or more, and filtered through a 0.22 μm filter (purchased from Millopore) for later transfection.

2. Cells Transfection:

293E cells (purchased from Invitrogen) were cultured in Freestyle 293 expression medium (purchased from Invitrogen) and the shaker used for culturing was set to 37° C., 130 RPM and 8% $CO_2$ (v/v). During transfection, the Freestyle 293 expression medium was added with 10% (v/v) F68 (purchased from Invitrogen) to a final concentration of 0.1% (v/v) of F68 to obtain Freestyle 293 expression culture containing 0.1% (v/v) F68, which was named medium A. 5 mL of medium A and 200 μg/mL of PEI (purchased from Sigma) were mixed to obtain medium B. 5 mL of the medium A and 100 μg/mL of the recombinant plasmid obtained in step (1) were mixed to obtain medium C. After 5 minutes, the medium B and the medium C were combined and mixed, and allowed to stand for 15 minutes to obtain a mixture D. 10 mL of the mixture D was slowly added to 100 mL of the Freestyle 293 expression medium containing 293E cells until the cell density of 293E reached $1.5 \times 10^6$/mL, and the mixture was shaken simultaneously to avoid excessive concentration of PEI and cultured in a shaker. Peptone was added the next day to a final concentration of 0.5% (w/v). On the 5th to 7th day, the antibody titer of the culture solution was measured. On the 6th to 7th day, the supernatant was collected by centrifugation (3500 RPM, 30 minutes), and filtered through a 0.22 μm filter to obtain a filtered cell supernatant for purification.

3. Antibodies Purification:

The continuously produced endotoxin-free column and Protein A packing (available from GE) were rinsed with 5 column volumes of 0.5 M NaOH and then equilibrated to neutrality with 5 column volumes of PBS (PBS buffer, pH 7.4). The filtered cell supernatant obtained in step (2) was loaded on the column, and the fluid flows were collected as necessary. After finishing the loading, the column was rinsed with 5 column volumes of PBS. Elution was carried out with 5 column volumes of 0.1 M Glycine-HCl, pH 3.0, and the eluate was collected and 0.1 volume of 1 M Tris-HCl (1.5 M NaCl) with pH 8.5 was immediately added to neutralized IL-13 antibody. All of the solutions used above required newly prepared. After harvesting the IL-13 antibody, dialysis was performed in 1×PBS for 4 hours to avoid endotoxin contamination. After finishing the dialysis, the concentration of the antibody was measured using a spectrophotometer or a kit, the purity of the antibody was determined using HPLC-SEC, and the endotoxin content of the antibody was detected using an endotoxin test kit (purchased from Lonza). Then the obtained IL-13 antibody was characterized. The human antibody hP4_4H12 and the chimeric antibodies c29D9H8, c28A2E11, c35E2C3, c70F10A10 and c35H6E1 were prepared by using the lead antibodies P4_4H12, 29D9H8,28A2E11, 35E2C3, 70F10A10 and 35H6E1, the letter h (human) at front-end of cloning number indicated a fully human antibody, and c (chimera) indicated a mouse-human chimeric antibody (hereinafter referred to as chimeric antibody).

Embodiment 8

Characterization of Chimeric Antibodies and Fully Human Antibodies

The mouse-human chimeric IL-13 antibodies or the fully human IL-13 antibodies obtained in Embodiment 7 were used for the following assay (the protocol was the same as that in Embodiment 5).

Figure 4:
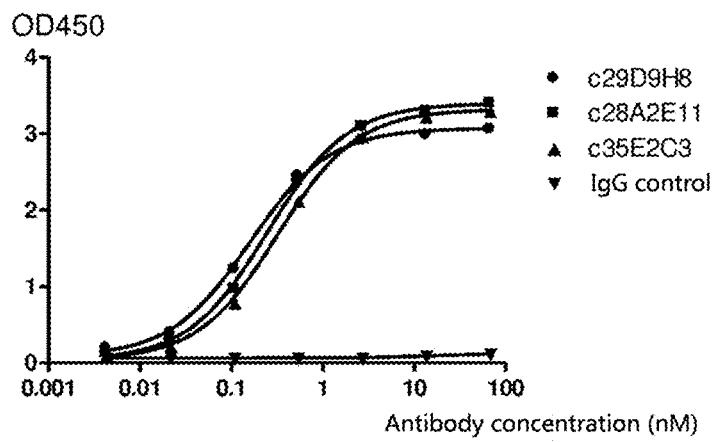
FIG. 4 shows the results of ELISA for detecting the reactivity of the chimeric antibody with the IL-13R130Q variant, where the abscissa 0 represents a blank control of 1% (w/w) BSA.

A. Detecting the Binding of Antibodies to Immunogen a, IL-13R130Q Variants and Cynomolgus IL-13 by ELISA The detailed protocols were the same as those in Embodiment 5, Test A. Some experimental results are shown in FIGS. 3-5 and Tables 19-21. Tables 19-21 illustrate that the above antibodies bind to recombinant human IL-13 protein, recombinant human IL-13R130Q variant, and recombinant cynomolgus IL-13 at the ELISA level. The IgG control is mouse IgG, and the data shown in the table are $OD_{450\,nm}$ values.

TABLE 19

1 ELISA detection of the reactivity of chimeric antibodies with immunogen A

| $OD_{450nm}$ | Antibody concentration (nM) | | | | | | | |
|---|---|---|---|---|---|---|---|---|
| Clone No. | 13.33 | 2.67 | 0.53 | 0.11 | 0.02 | 0.00 | 0.00 | 0.00 |
| c28A2E11 | 2.71 | 2.60 | 1.93 | 0.83 | 0.25 | 0.10 | 0.07 | 0.06 |
| c35E2C3 | 2.59 | 2.40 | 1.63 | 0.59 | 0.18 | 0.09 | 0.07 | 0.06 |
| IgG Control | 0.09 | 0.08 | 0.07 | 0.07 | 0.07 | 0.08 | 0.07 | 0.07 |

2 ELISA detection of the reactivity of fully human antibody with immunogen A

| $OD_{450nm}$ | Antibody concentration (nM) | | | | | | | |
|---|---|---|---|---|---|---|---|---|
| Clone No. | 333 | 67 | 13.3 | 2.7 | 0.53 | 0.11 | 0.021 | 0.004 |
| hP4_4H12 | 3.57 | 3.55 | 3.61 | 3.09 | 2.10 | 0.69 | 0.20 | 0.09 |
| IgG control | 0.16 | 0.08 | 0.06 | 0.06 | 0.06 | 0.05 | 0.05 | 0.05 |

TABLE 20

ELISA detection of the reactivity of chimeric antibodies with IL-13R130Q variant

| $OD_{450nm}$ | Antibody concentration (nM) | | | | | | |
|---|---|---|---|---|---|---|---|
| Clone No. | 66.67 | 13.33 | 2.67 | 0.53 | 0.11 | 0.021 | 0.004 |
| c29D9H8 | 3.06 | 2.99 | 2.92 | 2.46 | 1.23 | 0.40 | 0.20 |
| c35E2C3 | 3.40 | 3.30 | 3.10 | 2.40 | 0.97 | 0.28 | 0.13 |
| c35H6E1 | 3.31 | 3.23 | 2.97 | 2.13 | 0.80 | 0.23 | 0.11 |
| IgG control | 0.12 | 0.09 | 0.06 | 0.06 | 0.06 | 0.06 | 0.07 |

TABLE 21

ELISA detection of the reactivity of chimeric antibodies with cynomolgus IL-13 variant

| $OD_{450nm}$ | Antibody concentration (nM) | | | | | | | |
|---|---|---|---|---|---|---|---|---|
| Clone No. | 333.3 | 66.7 | 13.3 | 2.67 | 0.53 | 0.107 | 0.021 | 0.004 |
| c29D9H8 | 3.7 | 3.6 | 3.5 | 3.20 | 2.68 | 1.231 | 0.408 | 0.170 |
| c28A2E11 | 3.9 | 3.4 | 2.4 | 1.34 | 0.54 | 0.183 | 0.085 | 0.073 |
| c35E2C3 | / | 3.8 | 3.1 | 1.63 | 0.59 | 0.181 | 0.136 | 0.061 |
| IgG control | 0.2 | 0.1 | 0.1 | 0.06 | 0.08 | 0.059 | 0.068 | 0.061 |

B. Receptor-Ligand Binding-Inhibition Assay

Please refer to Part B of Embodiment 5 for the detailed protocols. Some experimental results are shown in FIGS. 10-11 and 22-23. Tables 22-23 show that IL-13 fully human antibodies and chimeric antibodies bind to human IL-13 and block the binding of human IL-13 to the cell surface receptor human IL-13Ra1/hIL-4Ra heterodimer, or block the binding of IL-13 to the cell surface human receptor IL-13Ra2. The IgG control is mouse IgG and the data in the table are the mean fluorescence intensity.

TABLE 22

1 FACS detection of chimeric antibodies blocking the binding of IL-13 to cell surface receptor IL-13Ra1/IL-4Ra heterodimer

| fluorescence intensity | Antibody concentration (nM) | | | | | | | |
|---|---|---|---|---|---|---|---|---|
| Clone No. | 166.67 | 33.33 | 6.67 | 1.33 | 0.27 | 0.05 | 0.01 | 0.002 |
| c29D9H8 | 20 | 20.2 | 28.3 | 45.7 | 72.6 | 90.3 | 101 | 105 |

TABLE 22-continued

| | | | | | | | | |
|---|---|---|---|---|---|---|---|---|
| c28A2E11 | 51.2 | 61.9 | 65.2 | 76.6 | 93 | 95.6 | 102 | 102 |
| c35E2C3 | 18.7 | 19.6 | 19.5 | 33.1 | 81.5 | 96.7 | 96.8 | 102 |
| c70F10A10 | 20.8 | 22.6 | 27.3 | 53.3 | 83.7 | 96.9 | 98.3 | 96 |
| IgG control | 109 | 108 | 106 | 104 | 100 | 106 | 104 | 102 |

2 FACS detection of fully human antibody blocking the binding of IL-13 to cell surface receptor IL-13Ra1/IL-4Ra heterodimer

| fluorescence intensity | Antibody concentration (nM) | | | | | | | |
|---|---|---|---|---|---|---|---|---|
| Clone No. | 166.67 | 33.33 | 6.67 | 1.33 | 0.27 | 0.05 | 0.01 | 0.002 |
| hP4_4H12 | 19.6 | 21.9 | 32.6 | 47.8 | 55.4 | 58.4 | 59 | 62.1 |
| IgG control | 61.7 | 56.5 | 58.5 | 60.3 | 58 | 56.4 | 59.2 | 60.3 |

TABLE 23

1 FACS detection of chimeric antibodies blocking the binding of IL-13 to cell surface receptor IL-13Ra2

| fluorescence intensity | Antibody concentration (nM) | | | | | | | |
|---|---|---|---|---|---|---|---|---|
| Clone No. | 166.67 | 33.33 | 6.67 | 1.33 | 0.27 | 0.05 | 0.01 | 0.002 |
| c29D9H8 | 20.4 | 22.8 | 25 | 34.6 | 56.3 | 81.6 | 95.9 | 101 |
| c28A2E11 | 58 | 64.8 | 65.7 | 77.7 | 92.9 | 97.8 | 99.1 | 102 |
| c35E2C3 | 19.3 | 20.3 | 22.2 | 29 | 63.8 | 90 | 98.1 | 99.1 |
| c70F10A10 | 24.6 | 27.8 | 31 | 49.1 | 78.4 | 94 | 97.6 | 97.5 |
| IgG control | 101 | 100 | 100 | 105 | 102 | 104 | 104 | 102 |

2 FACS detection of fully human antibody blocking the binding of IL-13 to cell surface receptor IL-13Ra2

| fluorescence intensity | Antibody concentration (nM) | | | | | | | |
|---|---|---|---|---|---|---|---|---|
| Clone No. | 166.67 | 33.33 | 6.67 | 1.33 | 0.27 | 0.05 | 0.01 | 0.002 |
| hP4_4H12 | 49.7 | 59.1 | 75.5 | 72.2 | 56.8 | 51.8 | 48.4 | 51.2 |
| IgG control | 45.1 | 43.8 | 43.9 | 46.2 | 46.5 | 46.1 | 48.5 | 47.4 |

C. TARC Secretion Assay

Please refer to the test section of Embodiment C for detailed protocols. Some experimental results are shown in FIG. 12 and Table 24. Table 24 shows that chimeric antibodies and fully human antibodies bind to human IL-13, and neutralize the TARC secretion of 549 cells induced by IL-13 and TNFα co-stimulation. The data shown in Table 24 are the concentration (pg/ml) of TARC in the culture supernatant, wherein the IgG control is mouse IgG.

confluency in a T-175 cell culture flask, culture medium was aspirated, and the cells were rinsed 1-2 times with PBS buffer. The cells were digested with trypsin-EDTA (purchased from Life Technology) and collected. After counting, the cells were diluted to $1 \times 10^5$ cells/mL with the culture medium, and aliquoted to a 96-well cell culture plate ($1 \times 10^4$ cells per well) at 100 μL per well. Then the plate was incubated overnight in a 5%. (v/v) $CO_2$ incubator at 37° C. On the second day, culture supernatant was aspirated from

TABLE 24

1 Chimeric human antibodies neutralized IL-13-induced TARC secretion

| TARC (pg/mL) | Antibody concentration (nM) | | | | | | | |
|---|---|---|---|---|---|---|---|---|
| Clone No. | 66.7 | 13.3 | 2.67 | 0.53 | 0.11 | 0.021 | 0.004 | 0.001 |
| c29D9H8 | 36 | 50 | 159 | 655 | 1847 | 2733 | 2953 | 3158 |
| c35E2C3 | 54 | 227 | 1091 | 2368 | 2607 | 3039 | 3152 | 3198 |
| c70F10A10 | 348 | 1121 | 2242 | 2800 | 2785 | 2774 | 3031 | 2610 |
| IgGcontrol | 2700 | 2820 | 2725 | 2840 | 2785 | 2998 | 2984 | 3116 |

2 Fully human antibody neutralized IL-13-induced TARC secretion

| TARC (pg/mL) | Antibody concentration (nM) | | | | | | | |
|---|---|---|---|---|---|---|---|---|
| Clone No. | 66.7 | 13.3 | 2.7 | 0.5 | 0.11 | 0.021 | 0.004 | 0.001 |
| hP4_4H12 | 339 | 1346 | 2529 | 2591 | 2762 | 2757 | 2457 | 339 |
| IgGcontrol | 2919 | 2866 | 2790 | 2581 | 2568 | 2583 | 2561 | 2919 |

D. Periostin Secretion Assay

Figure 13:
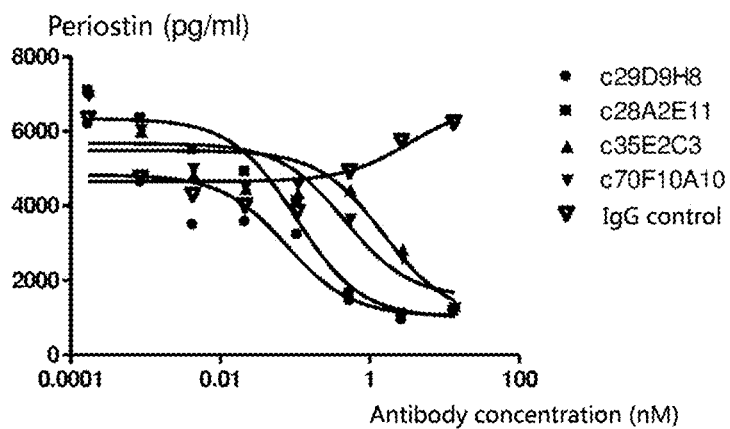
FIG. 13 is the results of IL-13-induced periostin secretion neutralized by chimeric antibody.

MRCS cells (purchased from ATCC) were cultured in EMEM medium (purchased from Gibco) containing 10% (w/w) fetal bovine serum and cultured at 37° C. under 5% (v/v) $CO_2$. After being expanded and cultured to 75-90% the plate, and the gradient dilutions of chimeric antibody prepared in Embodiment 7 was mixed with the immunogen A prepared in Embodiment 1 to obtain mixture C (the final concentration of immunogen A in mixture C was 5 ng/mL), and aliquoted into the culture plate. Next, the plate was incubated overnight in a 5% (v/v) $CO_2$ incubator at 37° C. After 20 hours, the concentration of periostin in the culture supernatant was determined using a periostin ELISA kit (purchased from RnD systems). The experimental protocol was carried out in accordance with the instructions of the kit. Some experimental results are shown in FIG. 13 and Table 25. Table 25 shows that the chimeric antibodies bind to human IL-13 and neutralize the secretion of periostin from MRC5 cells induced by human IL-13. The data in Table 25 are the concentration of periostin (pg/ml) in the culture supernatant, and the IgG control is mouse IgG.

TABLE 25

Lead antibody neutralized IL-13-induced secretion of periostin

| Periostin (pg/mL) | Antibody concentration ( nM ) | | | | | | | |
|---|---|---|---|---|---|---|---|---|
| Clone No. | 13.3 | 2.67 | 0.53 | 0.11 | 0.021 | 0.004 | 0.001 | 0.0002 |
| c29D9H8 | 1147 | 927 | 1447 | 3222 | 3568 | 3481 | 4633 | 6187 |
| c28A2E11 | 1161 | 1098 | 1652 | 4126 | 4922 | 5504 | 6346 | 7094 |
| c35E2C3 | 1347 | 2848 | 4456 | 4355 | 4479 | 4873 | 6021 | 7100 |
| c70F10A10 | 1261 | 2617 | 3658 | 4572 | 4538 | 5011 | 6049 | 6965 |
| IgGcontrol | 6238 | 5738 | 4924 | 3834 | 4010 | 4293 | 4756 | 6349 |

E, Vascular Cell Adhesion Molecule-1 (VCAM-1) Expression Experiment

Human umbilical vein endothelial cells (HUVEC) (purchased from AllCells) were cultured in HUVEC complete medium at 37° C. under 5% (v/v) $CO_2$. After being expanded and cultured to 75-90% confluency in T-175 flask, the medium was aspirated from culture and the cells were rinsed 1-2 times with PBS buffer. The cells were digested with trypsin-EDTA (purchased from Life Technology) and collected. After counting, the cells were diluted to $1.5 \times 10^5$ cells/mL with the culture medium, and aliquoted into the 384-well cell culture plates at 3000 HUVEC cells (20 µL) per well. The gradient dilutions of antibody prepared in Embodiment 7, the immunogen A prepared in Embodiment 1 and recombinant human TNFα were mixed at a volume ratio of 1:1:2 to obtain mixture D. Then mixture D was aliquoted into the culture plate at 20 µL per well to obtain mixture D', so that the volume ratio of the mixture D to the HUVEC cells in the culture plate was 1:1. In the end, the final concentration of recombinant human TNFα in the mixture D' was 25 ng/mL, and the final concentration of immunogen A was in the mixture D' was 0.5 ng/mL).

Figure 14:
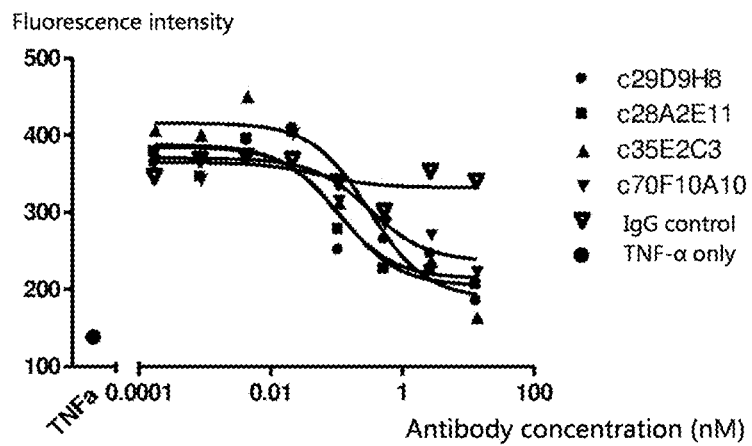
FIG. 14 is the results of IL-13-induced expression of vascular cell adhesion molecule-1 neutralized by chimeric antibody.

The cell culture plate was incubated overnight in a 5% (v/v) CO 2 incubator at 37° C. After 20 hours, supernatant was aspirated from the culture, and the mouse anti-human VCAM-1 (CD106) antibody (purchased from Biolegend) was diluted with the medium to a final concentration of 2 µg/mL, and aliquoted into the plate at 20 µL per well. Then the plate was incubated for 2 hours on ice, and rinsed 3 times with FACS buffer [PBS containing 2% (w/w) BSA]. Subsequently, a fluorescent (Alexa 488)-labeled donkey anti-mouse secondary antibody (purchased from invitrogen) was aliquoted to the plate at 20 µL per well, and the plate was incubated for 0.5-1.0 hour on ice. Then, a fixative [4% (w/w) paraformaldehyde] was aliquoted to the plate at 20 pt per well, and after 5-10 minutes, the plate was rinsed 3 times with PBS buffer. PI (purchased from invitrogen) and RNAse A (purchased from Qiagen) were diluted with PBS buffer to a final concentration of 9 nM and 200 ng/mL, respectively, and aliquoted into 384-well plates at 20 µL per well. The plate was incubated at 37° C. for 30 minutes. At last, the expression level of vascular cell adhesion molecule-1 (VCAM-1) on the cell surface was tested and analyzed by Acumen (microplate assay). Some experimental results are shown in FIG. 14 and Table 26. Table 26 shows that the chimeric antibodies bind to human IL-13 and neutralize the expression of vascular adhesion factor-1 on the surface of HUVEC cells induced by co-stimulation of human IL-13 and TNFα. The data shown in Table 26 are the mean fluorescence intensity of chimeric antibodies and IgG control; wherein the IgG control is mouse IgG; and TNFα represents the background value stimulated with TNFα alone without IL-13.

TABLE 26

Chimeric antibody neutralizes IL-13-induced expression of vascular cell adhesion molecule-1

| Fluorescence intensity | Antibody concentration (nM) | | | | | | | | |
|---|---|---|---|---|---|---|---|---|---|
| Clone No. | 13.3 | 2.67 | 0.53 | 0.11 | 0.021 | 0.004 | 0.001 | 0.0002 | 0 |
| 29D9H8 | 186 | 246 | 265 | 251 | 409 | 393 | 373 | 364 | — |
| 28A2E11 | 207 | 224 | 227 | 278 | 404 | 395 | 346 | 379 | — |
| 35E2C3 | 165 | 238 | 299 | 313 | 408 | 452 | 402 | 408 | — |
| 70F10A10 | 223 | 272 | 286 | 316 | 403 | 374 | 343 | 368 | — |
| IgG control | 341 | 354 | 302 | 340 | 369 | 373 | 369 | 347 | — |
| TNFα | — | — | — | — | — | — | — | — | 137 |

Embodiment 9

Inhibition of Respiratory Inflammation Induced by Human IL-13 in Mice by IL-13 Antibody Female Balb/c mice (8-12 weeks old, purchased from Shanghai Lingchang Biotechnology Co., Ltd.) were feed under SPF conditions after received, and the experiment was started after 1 week of adaptation. The mice were intraperitoneally injected with the chimeric antibodies, which were prepared in Embodiment 7 on the first day and the third day at 200 µL per animal (3 mg antibody per kilogram weight), with clone numbers of c29D9H8, c28A2E11 and c35E2C3 respectively. On the second and fourth days, each animal was stimulated and induced with 1 mg/mL immunogen A prepared in Embodiment 1 through 25 µL of airway spray. On the fifth day, all animals were tested for lung function using the FinePointe Whole Body Plethysmography System (DSI Buxco® FinePointe WBP System, purchased from DSI). Animals were atomized administration with methyl acetylcholine in a conscious and unconstrained state, and the airway narrowing index Penh (enhanced expiratory interval) was recorded by the instrument's own software (The detailed protocol of the assay was carried out according to the method described in the instruction manual of the instrument).

Figure 15:
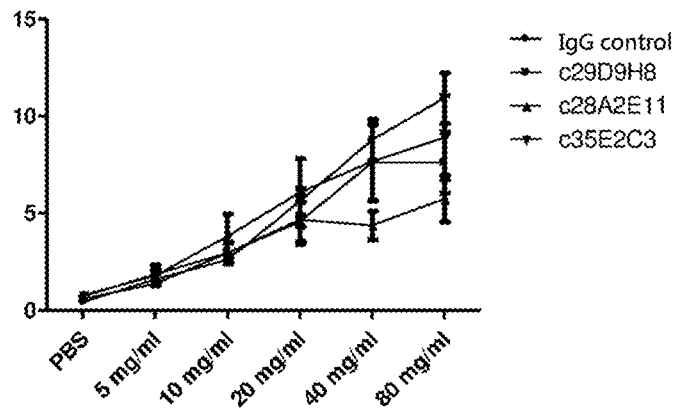
FIG. 15 is the results of experiment of chimeric antibody inhibiting human IL-13-induced respiratory inflammation in mice.

Some experimental results are shown in FIG. 15 and Table 27. Table 27 illustrates that mice induced high airway responsiveness under stimulation with human IL-13, or immunogen A, making them more sensitive to methyl acetylcholine stimulation, and an increasing penh values. The chimeric antibodies bind to human IL-13 and neutralize airway hyperresponsiveness induced by human IL-13. The data in the table are the airway narrowing index Penh, which represented airway hyperresponsiveness, and the IgG control is human IgG.

TABLE 27

Inhibition of respiratory inflammation induced by human IL-13 in mice

| penh | Methyl acetylcholine concentration (mg/mL) | | | | | |
|---|---|---|---|---|---|---|
| Clone No. | 0 | 5 | 10 | 20 | 40 | 80 |
| c29D9H8 | 0.59 | 1.37 | 2.95 | 4.56 | 7.61 | 7.62 |
| c28A2E11 | 0.72 | 1.85 | 2.96 | 4.67 | 4.38 | 5.75 |
| c35E2C3 | 0.78 | 1.78 | 3.82 | 6.06 | 7.67 | 8.90 |
| IgGcontrol | 0.43 | 1.59 | 2.61 | 5.62 | 8.78 | 10.94 |

Embodiment 10

Antibody Affinity Assay

Figure 16A:
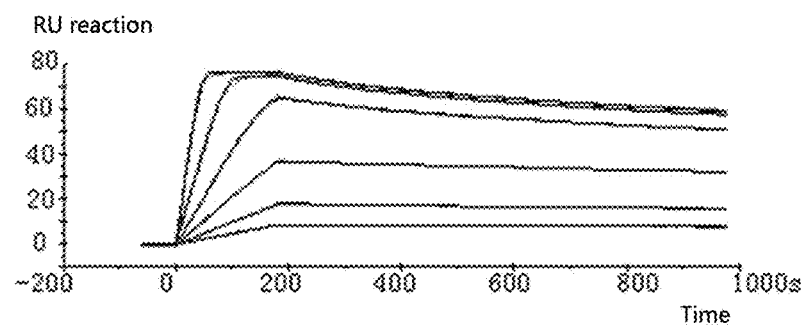
FIG. 16A shows the results of the affinity assay of chimeric antibody c29D9H8 and human IL-13, the concentrations of IL-13 from top to bottom in each curve are 12.5 nM, 6.25 nM, 3.125 nM, 1.5625 nM, 0.78125 nM and 0.390625 nM, respectively.
Figure 16B:
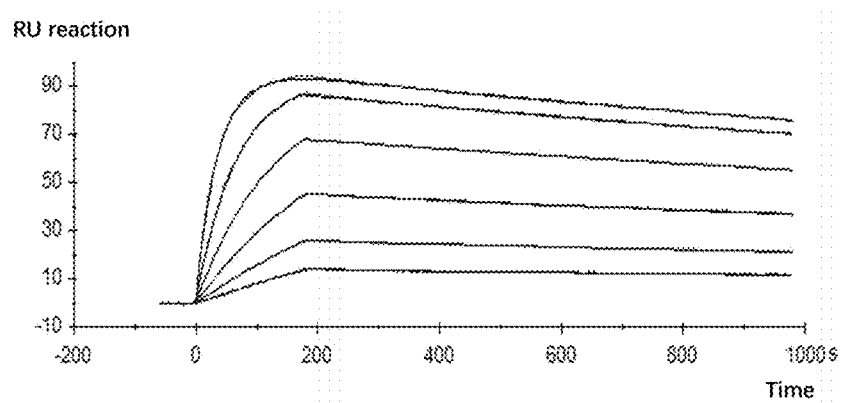
FIG. 16B shows the results of the affinity assay of chimeric antibody c35E2C3 and human IL-13, the concentration of IL-13 from top to bottom in each curve is 100 nM, 50 nM, 25 nM, 12.5 nM, 6.25 nM and 3.125 nM, respectively.

Anti-human Fc IgG (purchased from Geneway) was coupled to the surface of a CM5 chip (purchased from GE) to 6000-10000 RU by an amino coupling method, and FC1 was used as a reference channel. The protocol of coupling and fixation was as follows: the chip was activated with newly prepared mixture of 50 mM N-hydroxysuccinimide (NHS) and 200 mM 1-(3-dimethylaminopropyl)-3-ethylcarbodiimide salt (EDC) at a molar ratio of 1:1 for 7 minutes. Then, 10-50 µg/mL of anti-human Fc IgG diluted in 10 mM sodium acetate buffer (pH 5.0) was injected. The remaining activation sites were blocked with 1 M ethanolamine. Then, the chimeric antibodies prepared in Embodiment 7 were diluted to 5 µg/mL with HBS-EP-containing buffer (which can be appropriately adjusted depending on the capture level) and captured onto the chip at a flow rate of 10 µL/min to obtain a response value of approximately 100 to 300 RU. The purified immunogen A prepared in Embodiment 1 was then diluted to 100 nM (i.e., the highest concentration tentatively 100 nM) and flowed through the surface of the chip at a flow rate of 30 µL/min. Once sufficient signal values have been obtained, the purified immunogen A prepared in Embodiment 1 was diluted by several concentration gradients and flowed through the surface of the chip, respectively. At the end of each cycle, the surface of the chip was regenerated with 10 mM glycine at pH 1.5. The kinetic rate constants were then subtracted from the blank control and the data were fitted using 1:1 binding model through the global fit analysis method (refer to the Biacore operation manual). The dissociation equilibrium rate constant (KD) was calculated by the following formula: KD=kd/ka, where Kd was the dissociation constant and Ka was the binding constant. Some experimental results are shown in FIG. 16 and Table 28. Table 28 shows that the affinity of the chimeric antibody prepared in Embodiment 7 to human IL-13 is $KD<9\times10^{-8}$ M.

TABLE 28

Affinity results of antibodies and human IL-13

| Clone No. | ka (1/Ms) | kd (1/s) | KD (M) |
|---|---|---|---|
| c29D9H8 | $2.51 \times 10^7$ | $8.13 \times 10^{-4}$ | $3.24 \times 10^{-11}$ |
| c28A2E11 | $5.49 \times 10^5$ | $4.38 \times 10^{-3}$ | $7.98 \times 10^{-9}$ |
| c35E2C3 | $3.00 \times 10^5$ | $2.60 \times 10^{-4}$ | $8.63 \times 10^{-10}$ |
| c70F10A10 | $2.67 \times 10^5$ | $2.71 \times 10^{-4}$ | $1.02 \times 10^{-9}$ |
| c35H6E1 | $1.33 \times 10^6$ | $4.45 \times 10^{-4}$ | $3.36 \times 10^{-10}$ |

All references mentioned in the present invention are incorporated herein by reference, as if each reference was individually incorporated by reference. In addition, it is to be understood that those skilled in the art can make various changes or modifications to the present invention after reading the foregoing contents of the present invention, and these equivalent forms also fall within the scope of the appended claims of the present application.

What is claimed is:

1. An isolated protein comprising a heavy chain variable region of an anti-IL-13 antibody and a light chain variable region of an anti-IL-13 antibody, wherein the heavy chain variable region comprises a heavy chain CDR1, a heavy chain CDR2 and a heavy chain CDR3, and the light chain variable region comprises a light chain CDR1, a light chain CDR2, and a light chain CDR3, wherein
the heavy chain CDR1 comprises the amino acid sequence of SEQ ID NO:26, the heavy chain CDR2 comprises the amino acid sequence of SEQ ID NO:27 and the heavy chain CDR3 comprises the amino acid sequence of SEQ ID NO:28; and, the light chain CDR1 comprises the amino acid sequence of SEQ ID NO:30, the light chain CDR2 comprises the amino acid sequence of SEQ ID NO:31 and the light chain CDR3 comprises the amino acid sequence of SEQ ID NO:32.

2. The protein of claim 1, wherein
the heavy chain variable region comprises the amino acid sequence of SEQ ID NO:25 and the light chain variable region comprises the amino acid sequence of SEQ ID NO:29.

3. The protein of claim 1, wherein said protein further comprises a heavy chain constant region of the anti-IL-13 antibody and a light chain constant region of the anti-IL-13 antibody.

4. The protein of claim 3, wherein the heavy chain constant region of the antibody is a heavy chain constant region of a human or a mouse antibody, and the light chain constant region of the antibody is a light chain constant region of a human or a mouse antibody.

5. The protein of claim 4, wherein the heavy chain constant region of the antibody is a heavy chain constant region of a human antibody, and the light chain constant region of the antibody is a light chain constant region of a human antibody.

6. The protein of claim 1, wherein the protein is a monoclonal antibody, a full-length antibody protein, an antibody-antigen binding domain protein fragment, a bispecific antibody, a multispecific antibody, a single-chain antibody fragment, a single-domain or a single-region antibody of the anti-IL-13 antibody.

7. A method for the detection of cells overexpressing IL-13 protein, comprising contacting a protein of claim 1 with a test sample of cells in vitro, and detecting and quantitating binding of the protein to the test sample.

8. A composition for the detection of cells overexpressing IL-13 protein, wherein said composition comprises the protein of claim 1 as an active ingredient.

9. A pharmaceutical composition comprising the protein of claim 1 as an active ingredient and a pharmaceutically acceptable carrier.

10. A pharmaceutical composition, wherein said pharmaceutical composition comprises 0.01-99.99% of the protein according to claim 1 and 0.01-99.99% of pharmaceutical carrier, and the percentage is the mass percentage of the pharmaceutical composition.

11. A process for treating a disease associated with abnormal expression or dysfunction of IL-13 in a subject in need thereof, comprising administering an effective amount of a protein of claim 1 to the subject, wherein said disease associated with abnormal expression or dysfunction of IL-13 is bronchial asthma.

12. A process for treating a disease associated with abnormal expression or dysfunction of IL-13 in a subject in need thereof, comprising administering an effective amount of a pharmaceutical composition of claim 9 to the subject, wherein said disease associated with abnormal expression or dysfunction of IL-13 is bronchial asthma.

* * * * *